(12) United States Patent
Panzner et al.

(10) Patent No.: US 11,541,010 B2
(45) Date of Patent: *Jan. 3, 2023

(54) AMPHOTERIC LIPOSOMES COMPRISING IMINO LIPIDS

(71) Applicant: BioNTech Delivery Technologies GmbH, Halle (DE)

(72) Inventors: Steffen Panzner, Halle (DE); Evgenios Siepi, Frenaros (CY)

(73) Assignee: BioNTech Delivery Technologies GmbH, Halle (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/866,363

(22) Filed: May 4, 2020

(65) Prior Publication Data
US 2020/0330384 A1     Oct. 22, 2020

Related U.S. Application Data

(63) Continuation of application No. 16/051,728, filed on Aug. 1, 2018, now abandoned, which is a (Continued)

(30) Foreign Application Priority Data

Jul. 9, 2009   (EP) .................................. 09165106
Sep. 23, 2009  (EP) .................................. 09171102

(51) Int. Cl.
*A61K 9/127*     (2006.01)
*C12N 15/88*     (2006.01)
(Continued)

(52) U.S. Cl.
CPC .......... *A61K 9/1272* (2013.01); *C07C 233/36* (2013.01); *C07C 233/43* (2013.01); (Continued)

(58) Field of Classification Search
CPC ................................................. A61K 9/1272
See application file for complete search history.

(56) References Cited

U.S. PATENT DOCUMENTS 5,651,981 A   7/1997   Ashley et al.
5,965,434 A   10/1999  Wolff et al.
(Continued)

FOREIGN PATENT DOCUMENTS

DE    19753132 C5   7/1999
EP      685234 B1   5/2000
(Continued)

OTHER PUBLICATIONS

Yunching Chen et al. "Novel Cationic Lipid That Delivers siRNA and Enhances Therapeutic Effect in Lung Cancer Cells." Molecular Pharmaceutics, vol. 6 No. 3, pp. 696-705, published on web Mar. 6, 2009. (Year: 2009).*

(Continued)

*Primary Examiner* — Isaac Shomer
(74) *Attorney, Agent, or Firm* — Morrison & Foerster LLP

(57) ABSTRACT

The invention concerns lipid assemblies, liposomes having an outer surface comprising a mixture of anionic and cationic moieties; wherein at least a portion of the cationic moieties are imino moieties that are essentially charged under physiological conditions, and their use for serum resistant transfection of cells.

20 Claims, 6 Drawing Sheets

Figure 1:
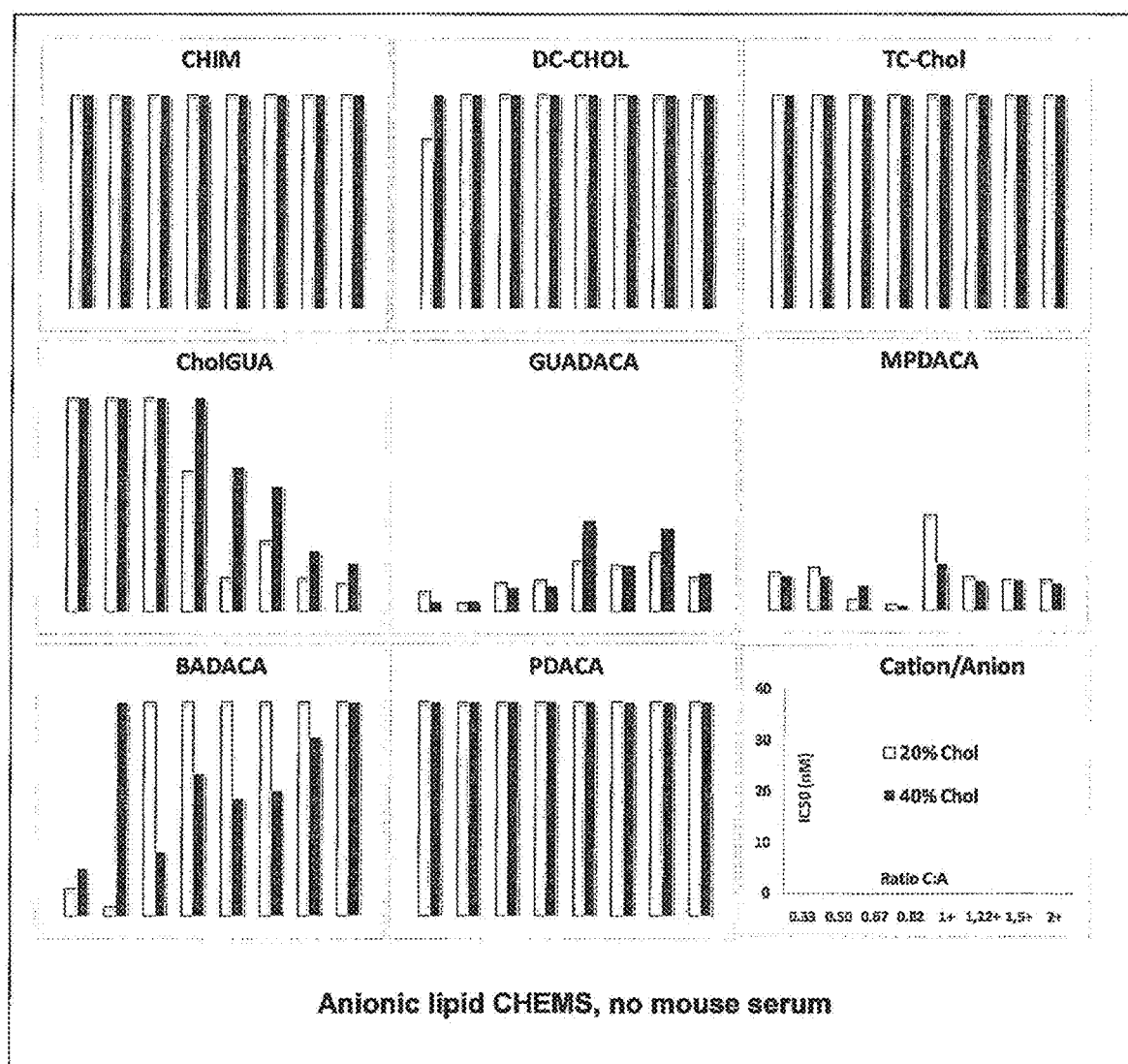
Figure 2:
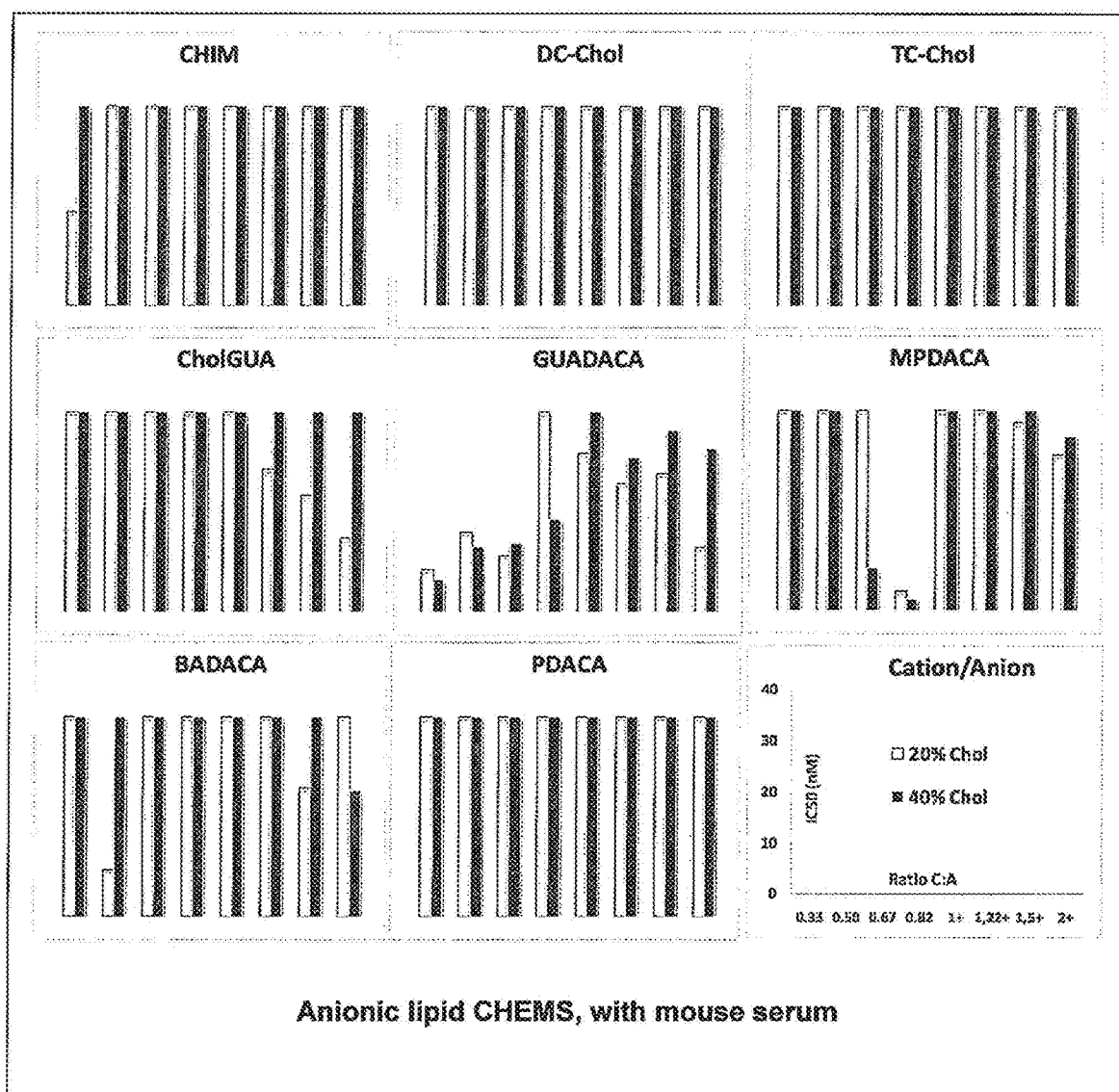
Figure 3:
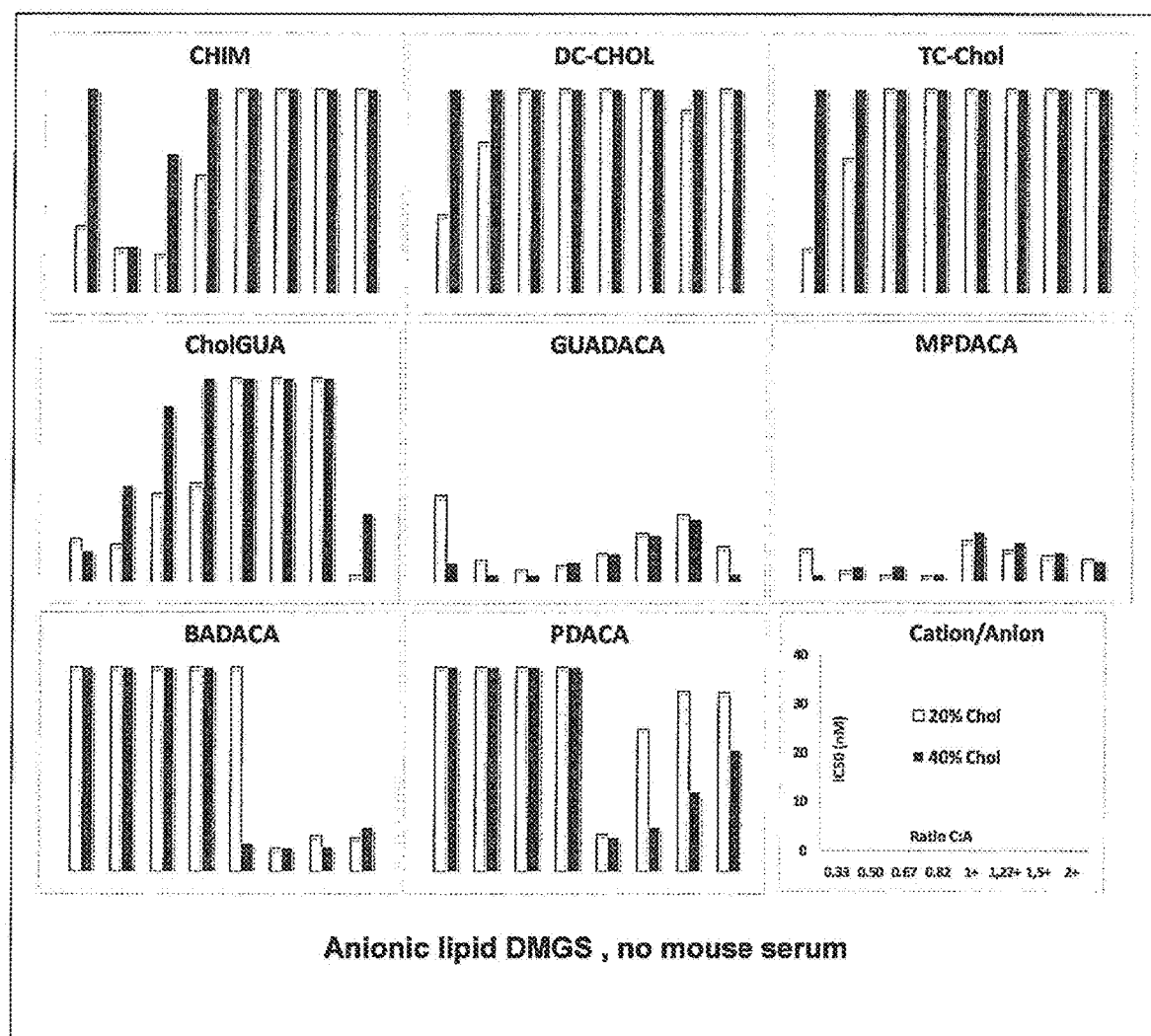
Figure 4:
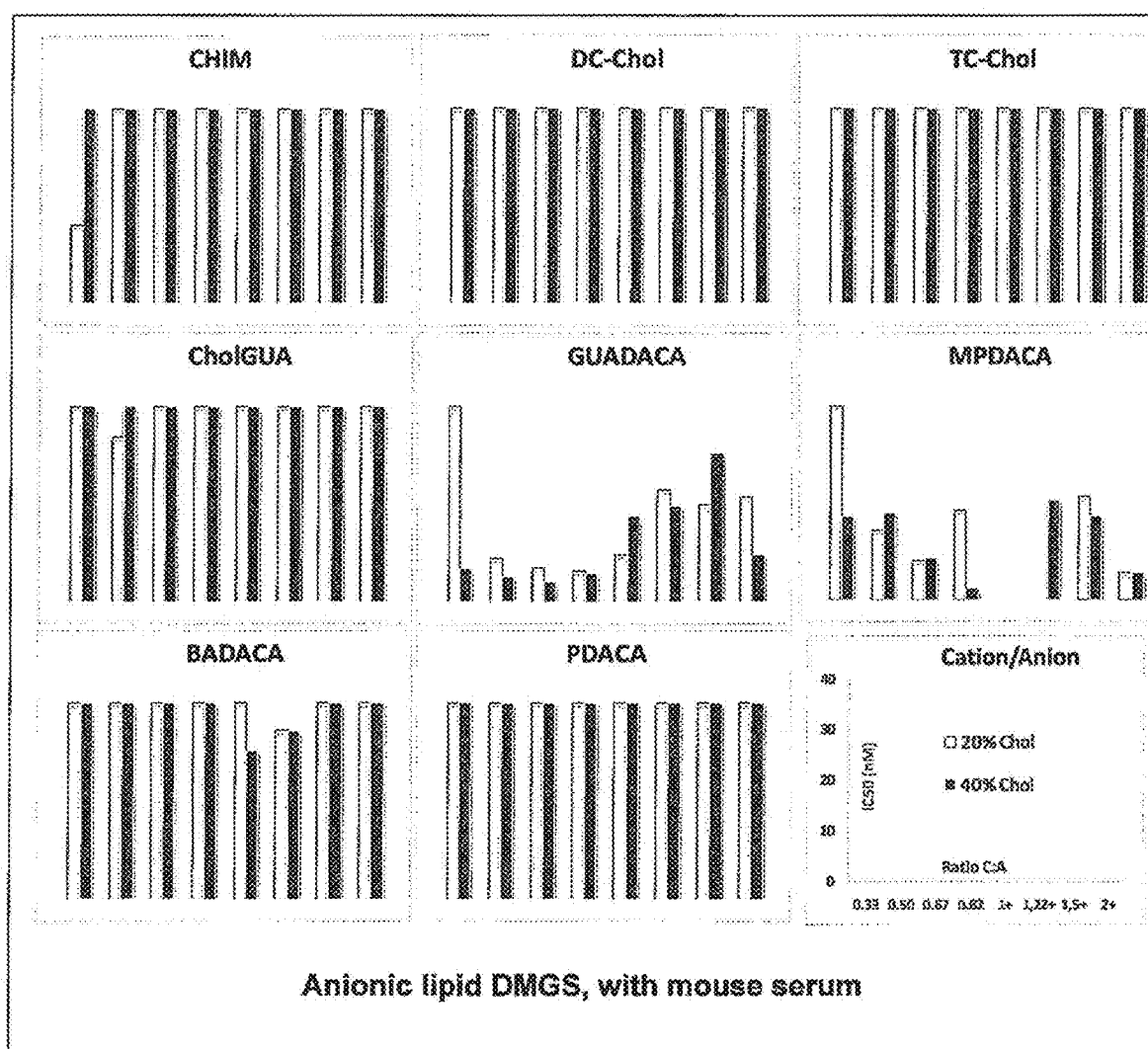
Figure 5:
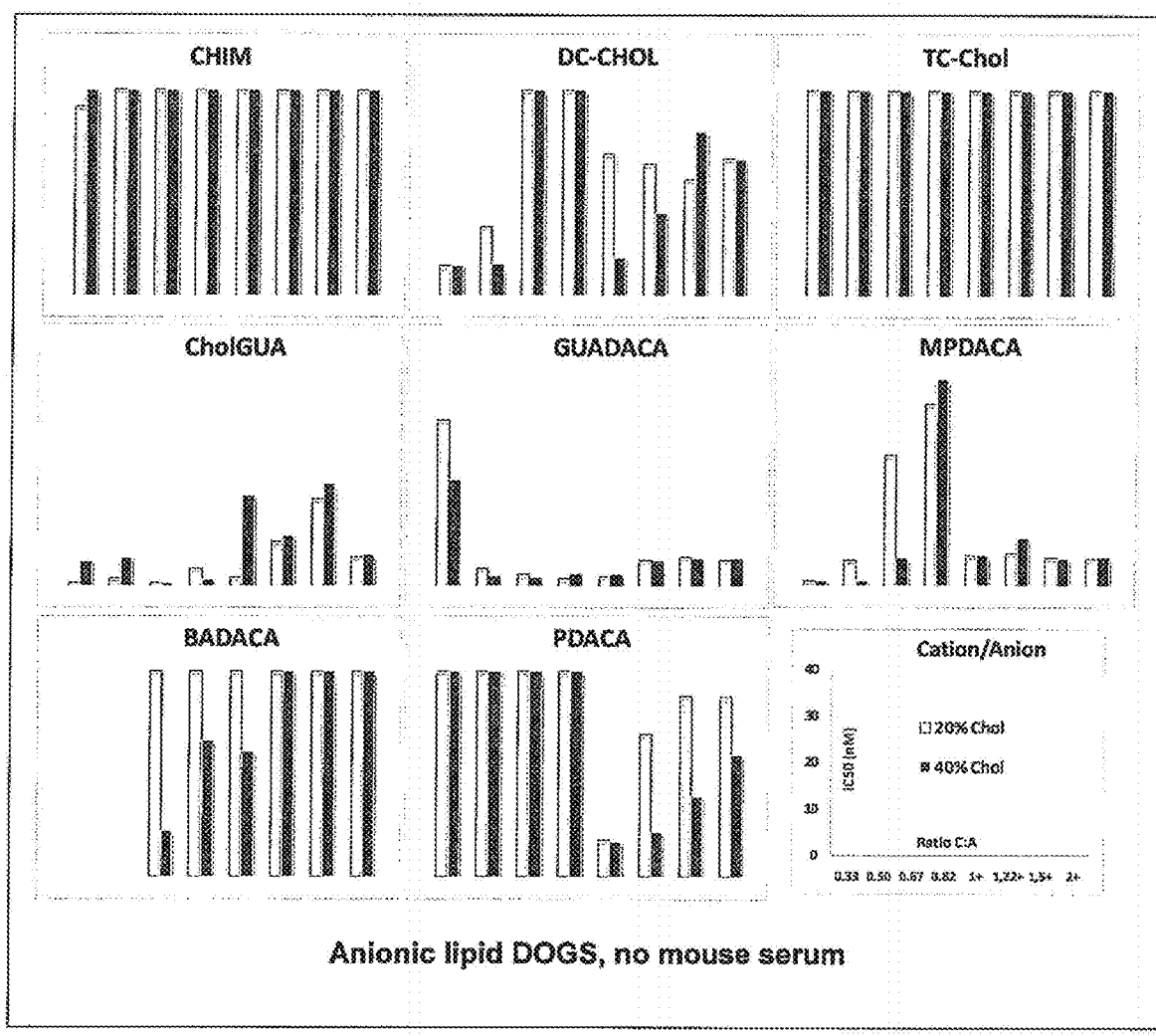
Figure 6:
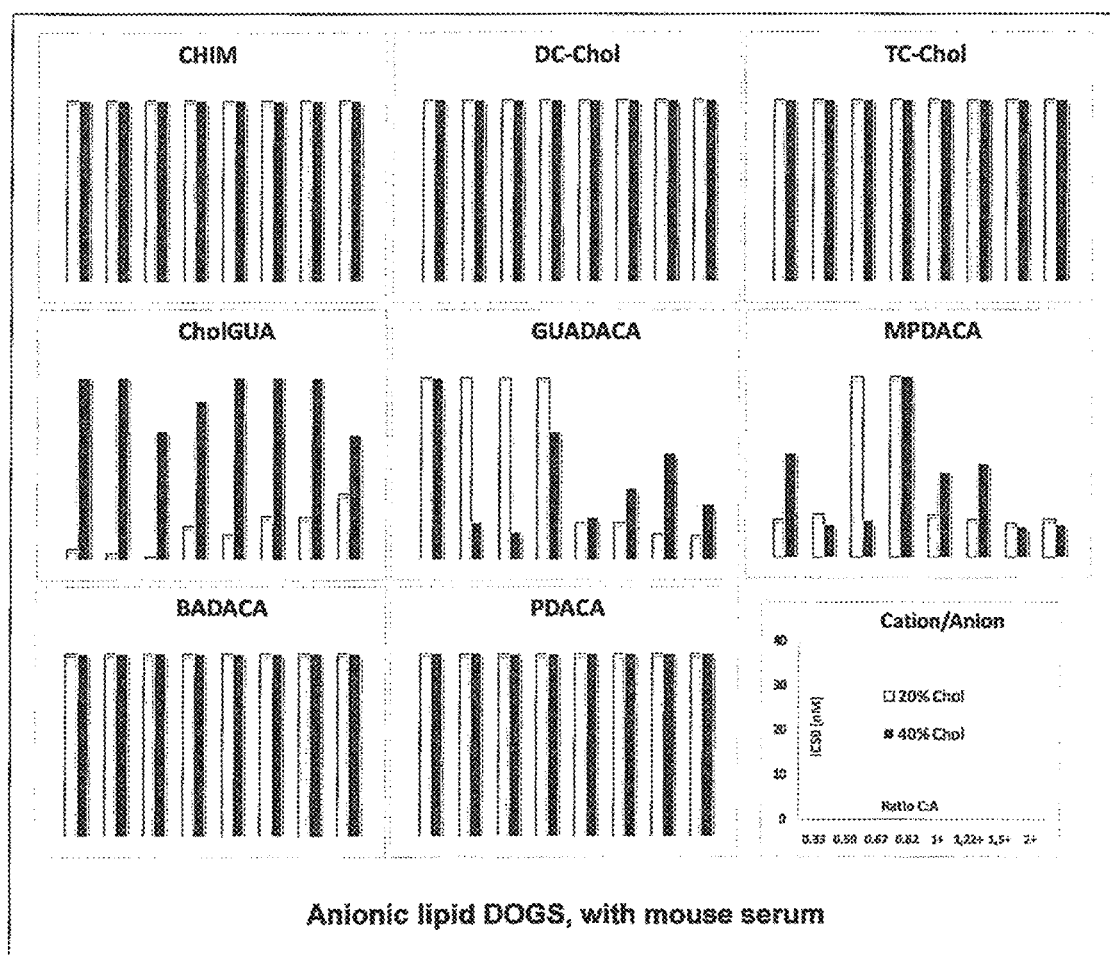

Related U.S. Application Data continuation of application No. 15/050,416, filed on Feb. 22, 2016, now Pat. No. 10,039,714, which is a continuation of application No. 13/378,484, filed as application No. PCT/EP2010/059487 on Jul. 2, 2010, now abandoned.

(51) Int. Cl.

| | |
|---|---|
| C07D 233/61 | (2006.01) |
| C07C 279/14 | (2006.01) |
| C07C 237/22 | (2006.01) |
| C07C 233/36 | (2006.01) |
| C07C 233/43 | (2006.01) |
| C07C 279/12 | (2006.01) |
| C07D 213/75 | (2006.01) |
| C07J 41/00 | (2006.01) |
| C12N 15/113 | (2010.01) |

(52) U.S. Cl.
CPC .......... *C07C 237/22* (2013.01); *C07C 279/12* (2013.01); *C07C 279/14* (2013.01); *C07D 213/75* (2013.01); *C07D 233/61* (2013.01); *C07J 41/0055* (2013.01); *C12N 15/1137* (2013.01); *C12N 15/88* (2013.01); *C12N 2310/14* (2013.01); *C12N 2320/32* (2013.01); *Y02P 20/582* (2015.11)

(56) References Cited

U.S. PATENT DOCUMENTS

| | | | | |
|---|---|---|---|---|
| 5,980,935 | A * | 11/1999 | Kirpotin | A61K 9/1271 |
| | | | | 424/450 |
| 6,034,137 | A * | 3/2000 | Belloni | C07C 237/06 |
| | | | | 514/477 |
| 6,171,862 | B1 | 1/2001 | Abe et al. | |
| 6,268,516 | B1 * | 7/2001 | Schneider | A61K 9/1272 |
| | | | | 554/105 |
| 6,287,591 | B1 | 9/2001 | Semple et al. | |
| 6,726,894 | B1 | 4/2004 | Engberts et al. | |
| 7,371,404 | B2 | 5/2008 | Panzner et al. | |
| 10,039,714 | B2 * | 8/2018 | Panzner | C07D 233/61 |
| 10,188,748 | B2 | 1/2019 | Von Der Mülbe et al. | |
| 2007/0252295 | A1 | 11/2007 | Panzner et al. | |
| 2008/0089932 | A1 * | 4/2008 | Panzner | A61K 9/1272 |
| | | | | 424/450 |

FOREIGN PATENT DOCUMENTS

| | | | |
|---|---|---|---|
| EP | 1392341 B1 | 3/2005 | |
| JP | 2007091657 A * | 4/2007 | |
| TW | I257924 * | 7/2006 | |
| TW | I257924 B | 7/2006 | |
| WO | WO-199601841 A1 | 1/1996 | |
| WO | WO-199743363 A1 | 11/1997 | |
| WO | WO-199805678 A2 | 2/1998 | |
| WO | WO-199821322 A1 | 5/1998 | |
| WO | WO-199932619 A1 | 7/1999 | |
| WO | WO-200155098 A1 | 8/2001 | |
| WO | WO-2002055693 A2 | 7/2002 | |
| WO | WO-2002066012 A2 | 8/2002 | |
| WO | WO-2008043575 A2 | 4/2007 | |
| WO | WO-2007064857 A2 | 6/2007 | |
| WO | WO-2007107304 A2 | 9/2007 | |
| WO | WO-2008137758 A2 * | 11/2008 | ............ A61P 25/00 |
| WO | WO-2009031896 A2 | 3/2009 | |
| WO | WO-2009047006 A2 | 4/2009 | |
| WO | WO-2009086558 A1 | 7/2009 | |
| WO | WO-2009116024 A2 | 9/2009 | |
| WO | WO-2009142892 A1 | 11/2009 | |

OTHER PUBLICATIONS

C-N Kuo et al. "A Novel Vector System for Gene Transfer into the Cornea Using a Partially Dried Plasmid Expressing 18 Basic Fibroblast Growth Factor-Synthetic Amphiphile." Current Eye Research, vol. 33, 2008, pp. 839-848. (Year: 2008).*

Wu-xiao Ding, Xian-rong Qi, Ping Li, Yoshie Maitani, Tsuneji Nagai. "Cholesteryl hemisuccinate as a membrane stabilizer in dipalmitoylphosphatidylcholine liposomes containing saikosaponin-d." International Journal of Pharmaceutics, vol. 300, 2005, pp. 38-47. (Year: 2005).*

Patrick Midoux, Chantal Pichon, Jean-Jacques Yaouanc and Paul-Alain Jaffrès. "Chemical vectors for gene delivery: a current review on polymers, peptides and lipids containing histidine or imidazole as nucleic acids carriers." British Journal of Pharmacology, vol. 157, 2009, pp. 166-178. (Year: 2009).*

Google Translate. English Translation of TWI257924B. Obtained from https://patents.google.com/patent/TWI257924B/en?oq=TWI257924B on May 4, 2021, originally published in Chinese on Jul. 11, 2006, 8 printed pages. (Year: 2006).*

Alexandros Pantos, Ioannis Tsogas, Constantinos M. Paleos. "Guanidinium group: A versatile moiety inducing transport and multicompartmentalization in complementary membranes." Biochimica et Biophysica Acta, vol. 1778 (2008), pp. 811-823. (Year: 2008).*

Marc Antoniu Ilies & Alexandru T Balaban. "Recent developments in cationic lipid-mediated gene delivery and gene therapy." Expert Opinion on Therapeutic Patents, vol. 11(11), 2001, pp. 1729-1752. (Year: 2001).*

English Translation of JP 2007091657 A. Obtained from https://patents.google.com/patent/JP2007091657A/en?oq=JP+2007-091657 on Jul. 28, 2022, originally published in Japanese on Apr. 12, 2007, 10 printed pages. (Year: 2007).*

Akinc et al., (2008). "A combinatorial library of lipid-like materials for delivery of RNAi therapeutics," Nat. Biotech., 26:561-569.

Akinc et al., (2010). "Targeted delivery of RNAi therapeutics with endogenous and exogenous ligand-based mechanisms," Mol. Ther., 18:1357-64.

Andreakos et al., (2009). "Amphoteric liposomes enable systemic antigen-presenting cell-directed delivery of CD40 antisense and are therapeutically effective in experimental arthritis," Arthritis Rheum., 60:994-1005.

Budker et al., (1996). "pH-sensitive, cationic liposomes: A new synthetic virus-like vector," Nat, Biotech., 14:760-764.

Chien at al., (2005). "Novel cationic cardiolipin analogue-based liposome for efficient DNA and small interfering RNA delivery in vitro and in vivo," Cancer Gene Ther., 12:321-8.

Cho-Chung et al., (1999). "Oligonucleotides as transcription factor decoys," Curr. Opin. Mol. Ther., 1:386-392.

De Fougerolles et al., (2007). "Interfering with disease: a progress report on siRNA-based therapeutics," Nat. Rev. Drug Discov., 6:443-453.

European Search Report received for Patent Application No. EP14188521, dated Nov. 12, 2014, 6 pages.

Hafez et al., (2000). "Tunable pH-sensitive liposomes composed of mixtures of cationic and anionic lipids," Biophys. J., 79(3):1438-1446.

Haupenthal et al., (2007). "RNAse A-like enzymes in serum inhibit the anti-neoplastic activity of siRNA targeting polo-like kinase 1," Int. J. Cancer, 121:206-210.

International Search Report and Written Opinion received for PCT Patent Application No. PCT/EP2010/059487, dated Jan. 13, 2011, 7 pages.

Kim et al., (2006). "Cholesteryl oligoargine delivering vascular endothelial growth factor siRNA effectively inhibits tumor growth in colon adenocarcinoma," Mol. Ther., 14:343-350.

Lai et al., (1985). "Acid- and calcium-induced structural changes in phosphatidylethanolamine membranes stabilized by cholesteryl hemisuccinate," Biochemistry, 24:1654-1661.

Mims et al., (1994). "A Nonexchangeable Apolipoprotein E Peptide That Mediates Binding to the Low Density Lipoprotein Receptor," J Biol. Chem., 269:20539-20547.

(56) References Cited

OTHER PUBLICATIONS

Morrissey et al., (2005). "Potent and persistent in vivo anti-HBV activity of chemically modified siRNAs," Nat. Biotech., 23:1-6.

Peer et al., (2008). "Systemic leukocyte-directed siRNA delivery revealing cyclin D1 as an anti-inflammatory target," Science, 319: 627-630.

Rensen et al., (1997). "Human Recombinant Apolipoprotein E-Enriched Liposomes Can Mimic Low-Density Lipoproteins as Carriers for the Site-Specific Delivery of Antitumor Agents," Mol. Pharmacol., 52:445-55.

Rensen et al., (1997). "Particle size determines the specificity of apolipoprotein E-containing triglyceride-rich emulsions for the LDL receptor versus hepatic remnant receptor in vivo," Lipid Res., 38:1070-1084.

Santel et al., (2006). "A novel siRNA-lipoplex technology for RNA interference in the mouse vascular endothelium," Gene Therapy, 13:1222-1234.

Sauer et al., (2005). "An apolipoprotein E-derived peptide mediates uptake of sterically stabilized liposomes into brain capillary endothelial cells," Biochemistry, 44:2021-9.

Semple et al., (2010). "Rational design of cationic lipids for siRNA delivery," Nat. Biotech., 28:172-176.

Shi et al., (2002). "Interference of poly(ethylene glycol)-lipid analogues with cationic-lipid-mediated delivery of oligonucleotides; role of lipid exchangeability and non-lamellar transitions," Biochem. J., 366:333-341.

Silvius et al., (1993). "Interbilayer transfer of phospholipid-anchored macromolecules via monomer diffusion," Biochemistry, 32:3153-3161.

Su et al., (2004). "A gene atlas of the mouse and human protein-encoding transcriptomes," Proc. Natl. Acad. Sci. U.S.A, 101 (16): 6062-7.

Versluis et al., (1999). "Stable Incorporation of a Lipophilic Daunorubicin Prodrug into Apolipoprotein E-Exposing Liposomes Induces Uptake of Prodrug via Low-Density Lipoprotein Receptor in Vivo," J Pharmacol., Exp. Ther., 289(1):1-7.

Webb et al., (1998). "Comparison of different hydrophobic anchors conjugated to poly(ethylene glycol): effects on the pharmacokinetics of liposomal vincristine," Biochim. Biophys. Acta, 1372:272-282.

Wheeler et al., (1999). "Stabilized plasmid-lipid particles: construction and characterization," Gene Ther, 6:271-281.

Chen et al., (2009). "Novel Cationic Lipid That Delivers siRNA and Enhances Therapeutic Effect in Lung Cancer Cells." Molecular Pharmaceutics, 6(3):696-705. Published on web Mar. 6, 2009.

Kuo et al., (2008). "A Novel Vector System for Gene Transfer into the Cornea Using a Partially Dried Plasmid Expressing 18 Basic Fibroblast Growth Factor-Synthetic Amphiphile," Current Eye Research, 33:839-848.

Allmann et al., (1972). "The molecular and crystal structure of 1,2-diazepines and their conformational mobility in solution," Tetrahedron, 28(3):581-595.

Dass, (2002). "Cytotoxicity issues pertinent to lipoplex-mediated gene therapy in-vivo," Journal Of Pharmacy And Pharmacology, 54:593-601.

Inoue et al., (1999). "Design of New Organic Gelators Stabilized by a Host-Guest Interaction," Journal of Organic Chemistry, 64:2933-2937.

Karmali et al., (2007). "Cationic liposomes as non-viral carriers of gene medicines: resolved issues, open questions, and future promises," Medicinal Research Reviews, 27(5):696-722.

Obata et al., (2008). "Evaluation of Cationic Assemblies Constructed with Amino Acid Based Lipids for Plasmid DNA Delivery," Bioconjugate Chemistry, 19(5):1055-1063. (abstract only).

Sochanik et al., (2000). "A new cholesterol derivative suitable for transfecting certain type of cells in the presence of 10% serum," Cancer Gene Therapy, 7(4):513-520.

Vigneron et al., (1996). "Guanidinium-cholesterol cationic lipids: efficient vectors for the transfection of eukaryotic cells," Proceedings of the National Academy of Sciences USA, 93(18):9682-9686.

Shi et al., (2002). "Efficient intracellular drug and gene delivery using folate receptor-targeted pH-sensitive liposomes composed of cationic/anionic lipid combinations," Journal of Controlled Release, 80:309-319.

* cited by examiner

AMPHOTERIC LIPOSOMES COMPRISING IMINO LIPIDS

CROSS REFERENCE TO RELATED APPLICATIONS

This application is a continuation application of U.S. application Ser. No. 16/051,728 filed Aug. 1, 2018, which is a continuation application of U.S. application Ser. No. 15/050,416 filed Feb. 22, 2016 (now U.S. Pat. No. 10,039, 714 issued Aug. 7, 2018), which is a continuation application of U.S. application Ser. No. 13/378,484 filed Jun. 8, 2012, which is a national stage application under 35 U.S.C. § 371 of International Application No. PCT/EP2010/059487 filed Jul. 2, 2010, which claims priority to EP 09165106.7 filed Jul. 9, 2009 and EP 09171102.8 filed Sep. 23, 2009.

FIELD OF THE INVENTION

The present invention relates to lipid assemblies or liposomes that are capable of overcoming a lipoprotein mediated uptake blockade. More specifically, this invention relates to improvements in liposomes comprising both negatively charged lipids having a carboxylic or phosphate head group and positively charged lipids having imino or guanido moieties or derivatives thereof in the respective polar regions.

BACKGROUND TO THE INVENTION

Liposomes have widespread use as carriers for active ingredients. Neutral or negatively charged liposomes are often used for the delivery of small molecule drugs, whereas positively charged (cationic) or the recently introduced class of amphoteric liposomes are mainly used for the delivery of nucleic acids such as plasmids or oligonucleotides. Important examples for cationic liposomes used for the delivery of nucleic acid cargoes include, but are not limited to Semple et al., Nat. Biotech. (2010) 28:172-176; Akinc et al., Nat. Biotech. (2008) 26:561-569; Chien et al., Cancer Gene Ther, (2005) 12:321-328; de Fougerolles, Nat. Rev. Drug Discov. (2007) 6:443-453; Kim et al., Mol. Ther. (2006) 14:343-350; Morrissey, Nat. Biotech. (2005) 23: 1002-1007; Peer, Science (2008) 319, 627-630 and Santel, Gene Ther. (2006) 13: 1222-1234. Application of amphoteric liposomes for the delivery of nucleic acids has been demonstrated in Andreak©s et al., Arthritis Rheum. (2009) 60:994-1005.

Amphoteric liposomes belong to the larger family of pH-sensitive liposomes, which further comprise pH-sensitive anionic or cationic liposomes, prototypes of which have been presented in Lai et al., Biochemistry (1985) 24:1654-1661 and Budker et al., Nat. Biotech. (1996) 14:760-764. Unlike the pH-sensitive anionic or cationic liposomes, amphoteric liposomes are complex structures and comprise at least a pair of lipids having complementary charge. WO 02/066012 discloses a key feature of amphoteric liposomes in that these have a stable phase at both low and neutral pH. WO 02/066012 and WO07/107304 describe a method of loading such particles with nucleic acids starting from a low pH.

Hafez, et al. (Biophys. J. 2000, 79(3), 1438-1446) and WO 02/066012 provide some guidance as to how to select lipid mixtures with truly amphoteric properties and more specifically how to determine their isoelectric point and onset of fusion. Neutral lipids can be additional constituents of amphoteric liposomes. The inclusion of one or more such neutral lipids significantly adds to the complexity of the mixture, especially since the individual amounts of all the components may vary. The very high number of possible combinations of lipids represents a practical hurdle towards a more rapid optimisation of amphoteric liposornes. In this regard, WO081043575 reveals strategies for the optimization of stability, fusogenicity and cellular transfection of amphoteric liposomes, particularly a method of predicting which mixtures of lipids form satisfactorily stable lamellar phases at high and low pH, whilst forming a fusogenic, hexagonal phase at an intermediate pH.

The amphoteric liposomes according to the abovementioned references are potent transfectants of cells. However, it was observed that the function of some of these liposomes could be blocked by the addition of certain sera, thereby potentially limiting the activity of these liposomes for the targeting of certain cells in vivo. This is further illustrated in the Examples presented herein, e.g., Example 3.

The inhibition of the uptake of amphoteric liposomes observed in different sera is apparently opposite to the recently published activation of cationic carrier through complex formation with lipoproteins, in this case ApoE, as demonstrated in Akinc et al., Mal. Ther, (2010) electronic publication on May 11th, ahead of print. DOI: 10.1038/mt.2010.85

A more detailed investigation revealed lipoproteins as mediators of this inhibitory effect. As shown in Example 4 herein, human serum deficient of lipoproteins is no longer able to inhibit the uptake of liposomes as indicated by the functional delivery of siRNA to the challenged cells. The inventors have now surprisingly and unexpectedly found that certain species of cationic imino lipids in combination with anionic lipids having a carboxyl or phosphate moiety in their polar head groups are particularly advantageous in maintaining transfection activity in the presence of serum. Frequently, a particular advantage was observed when the lipid assemblies or liposomes created from said lipid mixtures were formulated according to the method described herein and in WO081043575.

OBJECT OF THE INVENTION

It was therefore an object of the invention to provide lipid assemblies or liposomes that can transfect cells in the presence of various sera.

Another object of the invention is to provide pharmaceutical compositions comprising such liposomes as a carrier for the delivery of active agents or ingredients, including drugs such as nucleic acid drugs, e.g., oligonucleotides and plasmids into cells or tissues.

SUMMARY OF THE INVENTION

The present invention provides lipid assemblies, liposomes and their use for transfection of cells wherein said lipid assemblies comprise anionic and cationic amphiphiles and wherein at least a portion of the cationic amphiphiles are imino lipids that are substantially charged at pH7.5, and wherein the anionic amphiphiles are carboxyl or phosphate lipids and wherein further the charge ratio between the cationic and anionic amphiphiles is 1.5 or less.

In various embodiments of the invention, lipid assemblies comprising anionic and cationic amphiphiles are provided wherein at least a portion of the cationic amphiphiles are imino lipids that are substantially charged under physiological conditions, and wherein further at least a portion of the anionic amphiphiles are carboxyl lipids, and wherein the ratio between the cationic and anionic amphiphiles is lower or equal to 1.5.

In more specific aspects of the invention, lipid assemblies comprising a combination of lipids are provided wherein the cationic lipids of said combination comprise a guanido moiety and the anionic lipids of said combination comprise a carboxyl group, further characterized in that the ratio between the guanido moieties and the carboxyl groups is lower or equal to 1.5.

In other embodiments of the invention, lipid assemblies comprising anionic and cationic amphiphiles are provided wherein at least a portion of the cationic amphiphiles are imino lipids that are substantially charged under physiological conditions, and wherein further at least a portion of the anionic amphiphiles are phosphate lipids, and wherein the ratio between the cationic and anionic amphiphiles is lower or equal to 1.5. In further preferred aspects of such embodiments, the imino lipids are guanido lipids.

The charged imino groups of the cationic amphiphiles of the inventions have a pK of greater than 7.5 and are selected from imines, amidines, pyridines, 2-aminopyridines, heterocyclic nitrogen bases, guanido moieties, isoureas or thioisoureas. In preferred embodiments, the cationic lipids are selected from the group of PCNA, CHOLGUA, GUADACA, MPDACA or SAINT-18.

In preferred embodiments, the anionic lipids are selected from the group of CHEMS, DMGS, DOGS, DOPA or POPA.

In many embodiments, the lipid assemblies of the invention are liposomes.

In further embodiments, the lipid assemblies also comprise neutral lipids such as cholesterol, phosphatidylcholine, phosphatidylethanolamine or sphingomyelin or mixtures thereof.

In preferred embodiments the neutral lipid is cholesterol and the molar fraction of cholesterol in the lipid mixture is between 10 and 50 mol %.

In some embodiments, the lipid assemblies also comprise PEGylated lipids and in preferred aspects of such embodiments the liposomes are produced by a process comprising the steps of (i) formation and sealing of the liposomes in the presence of an active ingredient and (ii) a separate addition of PEG-lipids after said step (i).

It was unexpectedly found that serum resistant transfection can be achieved with lipid assemblies or liposomes having an outer surface comprising a mixture of anionic and cationic moieties; wherein at least a portion of the cationic moieties are imino moieties that are essentially charged under physiological conditions. In numerous embodiments, the lipid assemblies and liposomes of the present invention are formulated using a method described in WO03/043575 and also described in more detail herein.

DETAILED DESCRIPTION OF THE INVENTION

Lipid Chemistry

By "chargeable" is meant that the amphiphile has a pK in the range between 4 to pH 8. A chargeable amphiphile may therefore be a weak acid or base, "Stable" in connection with charged amphiphiles means a strong acid or base with a pK outside this range, which results in substantially stable charge on the range pH 4 to pH 8.

By "amphoteric" herein is meant a substance, a mixture of substances or a supra-molecular complex (e.g., a liposome) comprising charged groups of both anionic and cationic character wherein:
1) at least one, and optionally both, of the cation and anionic amphiphiles is chargeable, having at least one charged group with a pK between 4 and 8,
2) the cationic charge prevails at pH 4, and
3) the anionic charge prevails at pH 8.

As a result the substance or mixture of substances has an isoelectric point of neutral net charge between pH 4 and pH 8. Amphoteric character is by this definition different from zwitterionic character, as zwitterions do not have a pK in the range mentioned above. In consequence, zwitterions are essentially neutrally charged over a range of pH values; phosphatidylcholines and phosphatidylethanolamines are neutral lipids with zwitterionic character.

By "charge ratio" or "C/A" herein is meant the absolute value or modulus of the ratio between the nominal charges usually assigned to the cationic and anionic amphiphiles, respectively.

The nominal charge of a carboxyl group is "−1", that of a phosphate moiety is "−2" and the nominal charge of an imino compound is "+1". The "charge ratio" in a given mixture of amphiphiles or in a lipid assembly is then calculated from the product of these nominal charges and the respective molar fractions of the compounds considered, neutral compounds such as cholesterol or zwitterionic amphiphiles such as POPC or DOPE are not taken into account.

$$C/A = (x_{c1}*z_{c1} + x_{c2}*z_{c2} + \ldots x_{cn}*z_{cn})/(x_{a1}*z_{a1} + x_{a2} + \ldots x_{an}*z_{an})$$

Wherein $x_{c1 \ldots n}$ represents the molar fraction of a given cationic compound, represents the molar fractions of anionic compounds, $z_{c1 \ldots n}$ stands for the nominal charge of a given cationic compound and $z_{a1 \ldots n}$ represents the nominal charge of the anionic compound.

As an example, a mixture comprising 42 mol % of a carboxyl lipid, 38% of an imino lipid and 20 mol % of a neutral lipid has a charge ratio or C/A of 38/42=0.91. Another mixture comprising 27% of a phosphate lipid. 43 mol % of an imino lipid and 30 mol % of a neutral lipid has a charge ratio or C/A of 43/54=0.8 due to the double nominal charge of the phosphate group.

It becomes apparent from the definition and examples, that molar ratios or—for the sake of brevity—ratios between lipids and charge ratios have the same meaning for single-charged species and that these terms can be mutually exchanged within that group. This is for example the case for combinations of imino and carboxy lipids. In contrast to that, the molar ratio is different from the charge ratio for phosphate lipids, since these compounds may bear a double charge, e.g. In cases where the phosphate group is present as a primary phosphate ester as in DOPA. As shown in the calculation example above, the molar ratio or lipid ratio is then double the charge ratio. For the sake of clarity only, the term "charge ratio" is used with preference throughout this disclosure.

By "physiological pH" or "physiological conditions" herein is meant a pH of about 7.5.

Anionic lipids comprising carboxyl moieties in their polar head groups are well known to the skilled artisan. Examples of anionic lipids comprising carboxyl moieties in the polar head groups can be selected from the structures (1)-(4) below,

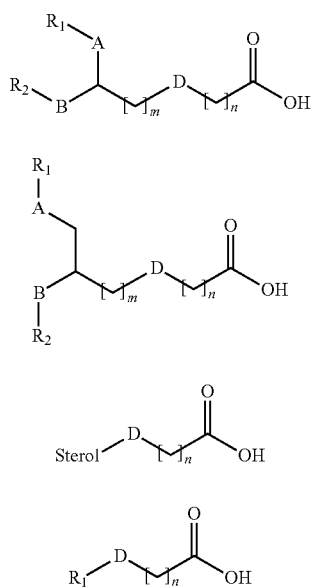

wherein n or m is an integer between 0 and 29, $R_1$ and $R_2$ are independently from each other an alkyl, alkenyl or alkinyl moieties having between 8 and 24 carbon atoms and 0, 1 or 2 unsaturated bonds, A, B or D are independently from each other absent, —$CH_2$—, —CH=, =CH—, —O—, —NH—, —C(O)—O—, —O—C(O)—, —C(O)—NH—, —NH—C(O)—, —O—C(O)—NH—, —NH—C(O)—O—, a phosphoric or phosphorous acid diester, and "sterol" can be a cholesterol attached via its C3 atom.

| | |
|---|---|
| CHEMS | Cholesterolhemisuccinate |
| Chol-COOH or Chol-C1 | Cholesteryl-3-carboxylic acid |
| Chol-C2 | Cholesterolhemioxalate |
| Chol-C3 | Cholestarolhemimalonate |
| Chol-C3N | N-(Cholesteryl-oxycarbonyl)glycine |
| Chol-C5 | Cholesterolhemiglutarate |
| Chol-C6 | Cholesterolhemiadipate |
| Chol-C7 | Cholesterolhemipimelate |
| Chol-C8 | Cholesterolhemisuberate |
| Chol-C12 | Cholesterolhemidodecane dicarboxylic acid |
| Chol-C13N | 12-Cholesteryloxycarbonylaminododecanoic acid |
| Chol-C16 | Cholesterolhemihexadecane dicarboxylic acid |

Cholesterolhemidicarboxylic acids and Cholesteryloxycarbonylaminocarboxylic acids of following general formula:

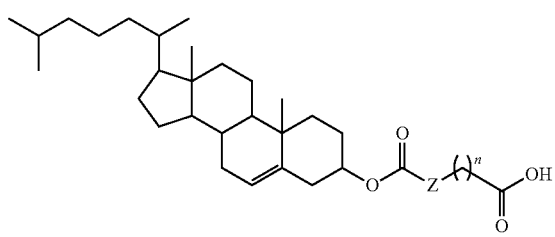

wherein Z is C or —NH— and n is any number between 0 and 29.

| | |
|---|---|
| DGS or DG-Succ | Diacylglycerolhemisuccinate (unspecified membrane anchor) |
| DOGS or DOG-Succ | Dioleoylglycerolhemisuccinate |
| DMGS or DMG-Succ | Dimyristoylglycerolhemisuccinate |
| DPGS or DPG-Succ | Dipalmitoylglycerolhemisuccinate |
| DSGS or DSG-Succ | Distearoylglycerolhemisuccinate |
| POGS or POG-Succ | 1-Palmitoyl-2-oleoylglycerol-hemisuccinate |
| DOGM | Dioleoylglycerolhemimalonate |
| DOGG | Dioleoylglycerolhemiglutarate |
| DOGA | Dialeoylglycerolhemiadipate |
| DMGM | Dimyristoylglycerolhemimalonate |
| DMGG | Dimyristoylglycerolhemiglutarate |
| DMGA | Dimyristoylglycerolhemiadipate |
| DOAS | 4-{(2,3-Dioleoyl-propyl)amino}-4-oxobutanoic acid |
| DOAM | 3-{(2,3-Dioleoyl-propyl)amino}-3-oxopropanoic acid |
| DOAG | 5-{(2,3-Dioleoyl-propyl)amino}-5-oxopentanoic acid |
| DOAA | 6-{(2,3-Dioleoyl-propyl)amino}-6-oxohexanoic acid |
| DMAS | 4-{(2,3-Dimyristoyl-propyl)amino}-4-oxobutanoic acid |
| DMAM | 3-{(2,3-Dimyristoyl-propyl)amino}-3-oxopropanoic acid |
| DMAG | 5-{(2,3-Dimyristoyl-propypamino}-5-oxopentanoic acid |
| DMAA | 6-{(2,3-Dimyristoyl-propyl)amino)-6-oxohexanoic acid |
| DOP | 2,3-Dioleoyl-propanoic acid |
| DOB | 3,4-Dioleoyl-butanoic acid |
| DOS | 5,6-Dioleoyl-hexanoic acid |
| DOM | 4,5-Dioleoyl-pentancic acid |
| DOG | 6,7-Dioleoyl-heptancic acid |
| DOA | 7,8-Dioleoyl-octanoic acid |
| DMP | 2,3-Dimyristoyl-propanoic acid |
| DMB | 3,4-Dimyristoyl-butanoic acid |
| DMS | 5,6-Dimyristoyl-hexanoic acid |
| DMM | 4,5-Dimyristoyl-pentanoic acid |
| DMG | 6,7-Dimyristoyl-heptanoic acid |
| DMA | 7,8-Dimyristoyl-octanoic acid |
| DOG-GluA | Dioleoylglycerol-glucuronic acid (1-or 4-linked) |
| DMG-GluA | Dimyristoylglycerol-glucuronic acid (1-or 4-linked) |
| DO-cHA | Dioleoylglycerolhemicyclohexane-1,4-dicarboxylic acid |
| DM-cHA | Dimyristoylglycerolhemicyclohexane-1,4-dicarboxylic acid |
| PS | Phosphatidylserine (unspecified membrane anchor) |
| DOPS | Dioleoylphosphatidylserine |
| DPPS | Dipalmitoylphosphatidylserine |
| MA | Myristic Acid |
| PA | Palmitic Acid |
| OA | Oleic Acid |
| LA | Linoleic Acid |
| SA | Stearic Acid |
| NA | Nervonic Acid |
| BA | Behenic Acid |
| POGA | Palmitoyl-oleoyl-glutamic acid |
| DPAA | Dipalmitoylaspartic acid |

Any dialkyl derivatives of the anionic lipids comprising diacyl groups listed above are also within the scope of the present invention.

Preferred anionic lipids having a carboxyl group can be selected from the group of Cho-CI to Chol-C16 including all its homologues, in particular CHEMS. Also preferred are the anionic lipids DMGS, DPGS, DSGS, DOGS, POGS.

Anionic lipids comprising phosphate moieties in their polar head groups are well known to the skilled artisan. Examples for phosphate lipids can be selected from structures (P1)-(P4) below.

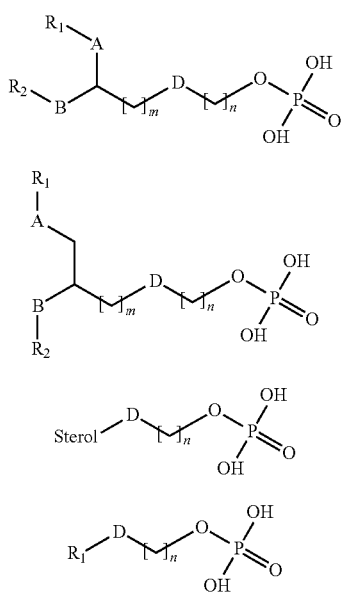

wherein n or m is an integer between 0 and 29, $R_1$ and $R_2$ are independently from each other an alkyl, alkenyl or alkinyl moieties having between 8 and 24 carbon atoms and 0, 1 or 2 unsaturated bonds, A, B or D are independently from each other absent, —$CH_2$—, —CH═, ═CH—, —O—, —NH—, —C(O)—O—, —O—C(O)—, —O(O)—NH—, —NH—C(O)—, —O—C(O)—NH— or —NH—C(O)—O— and "sterol" can be a cholesterol attached via its C3 atom.

The list below provides further specific examples of lipids carrying a phosphatidic acid group.

| | |
|---|---|
| Chol-P | Cholesterol-3-phosphate |
| DOPA | Dioleoyl-phosphatidic acid |
| POPA | Palmitoyl-oleoyl-phosphatidic acid |
| DPPA | Dipalmitoyl-phosphatidic acid |
| DMPA | Dimyristoylphosphatidic acid. |

Cetylphosphate or phosphoric acid ester homologues with R1 having between 16 and 24 carbon atoms.

The cationic lipids that can be used with this invention are amphipathic molecules comprising an imino moiety in their polar head group, wherein such imino moiety is substantially charged under physiological conditions. Therefore, in preferred embodiments the pK value of this functional group is 7.5 or greater, in further preferred forms the pK value of the imino group is 8.5 of higher. Imino moieties having such characteristics can be imines itself or be park of larger functional groups, such as amidines, pyridines, 2-aminopyridines, heterocyclic nitrogen bases, guanido functions, isoureas, isothioureas and the like.

The following structures (I1) . . . (I113) represent some specific examples of such imino moieties,

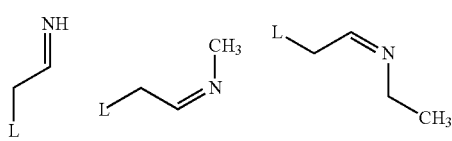

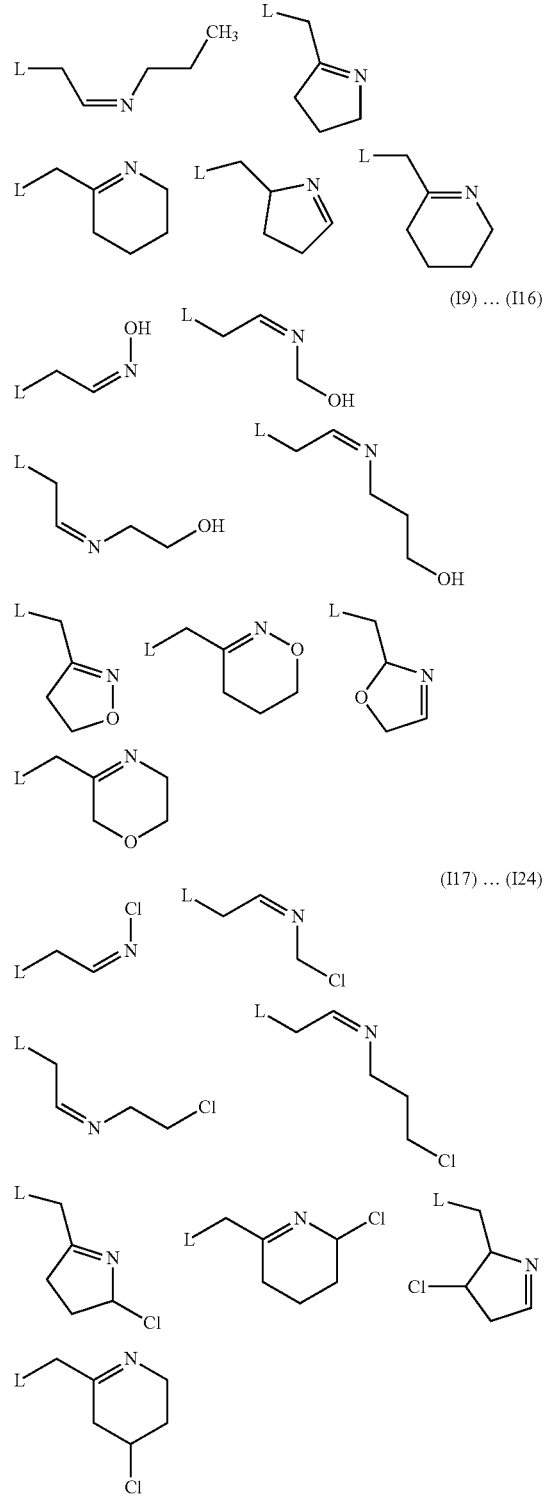

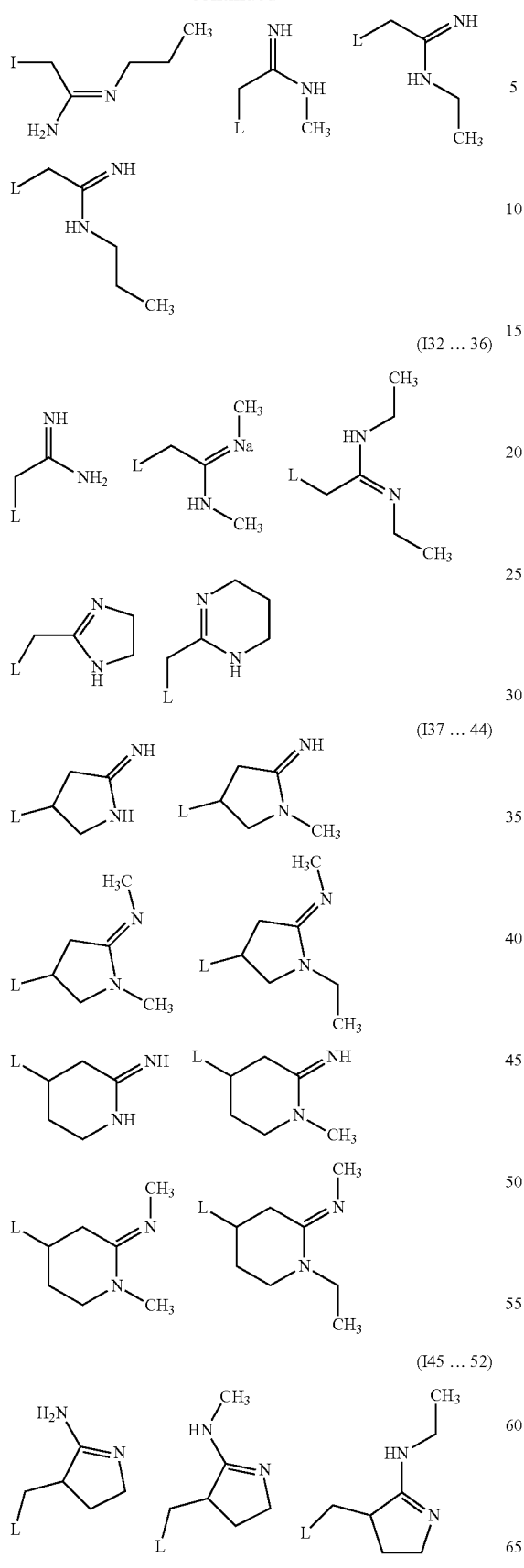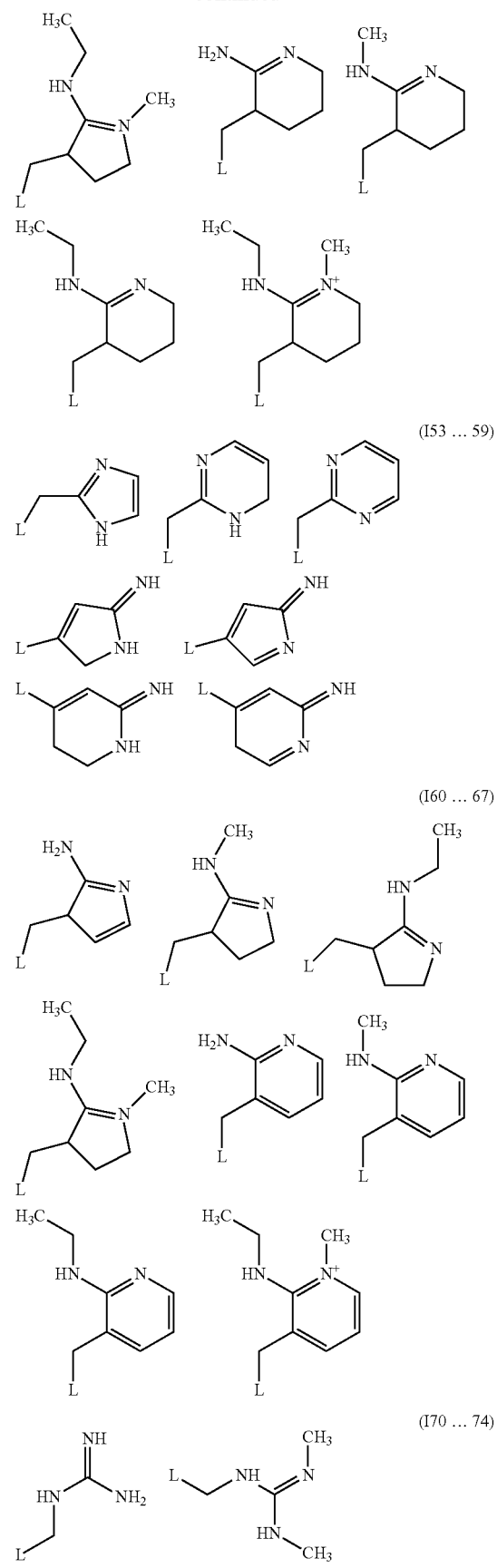

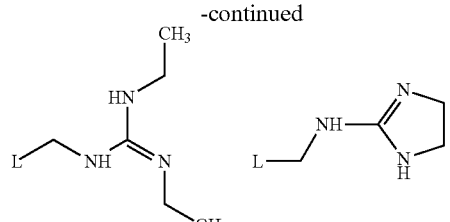
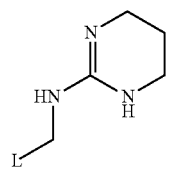
(I75 ... 82)
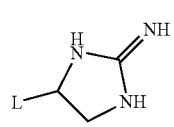
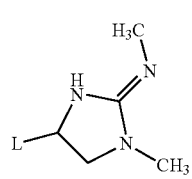
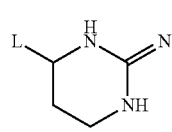
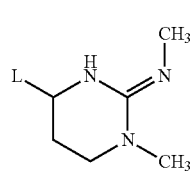
(I83 ... 90)
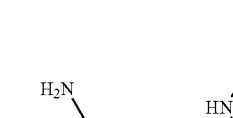
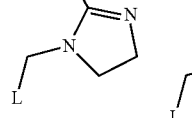
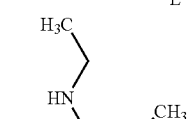
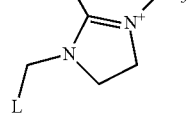
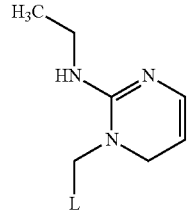
(I91 ... 97)
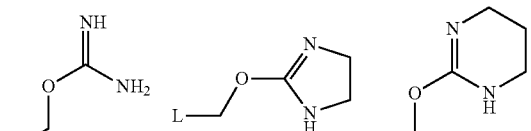
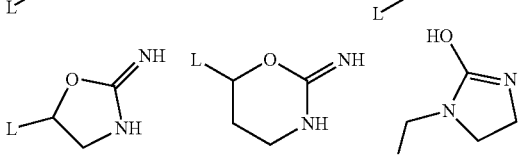
(I100 ... 106)
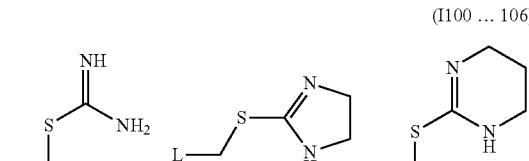
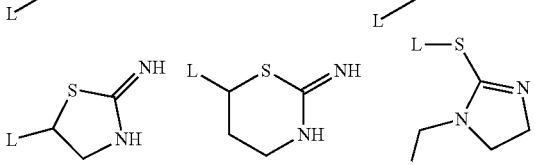
(I107 ... 113)
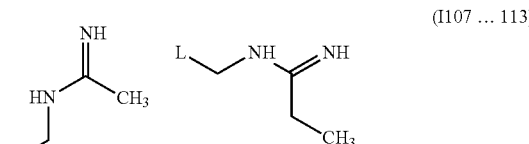
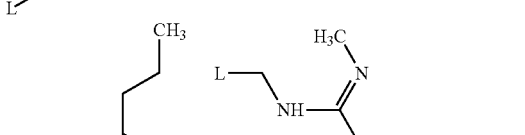
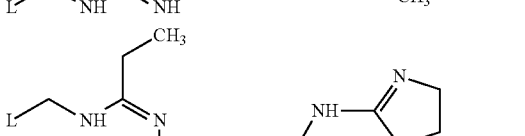
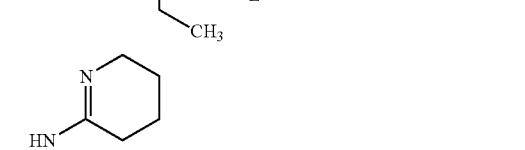

wherein L represents the apolar region and optionally linker or spacer moieties of the amphipathic lipid molecule. Examples of L can further be selected from the following general structures (11) to (15),

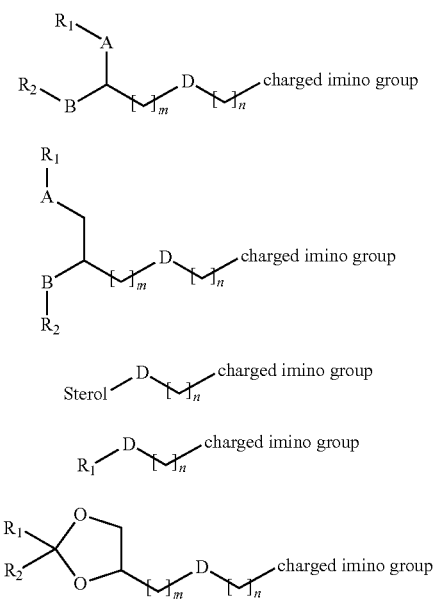

wherein n or m represent an integer between 0 and 29, $R_1$ and $R_2$ are independently from each other an alkyl, alkenyl or alkinyl moieties having between 8 and 24 carbon atoms and 0, 1 or 2 unsaturated bonds, A, B or D are independently from each other absent, —CH2—, —CH=, =CH—, —O—, —NH—, —C(O)—O—, —O—C(O)—, —C(O)—NH—, —NH—C(O)—, —O—C(O)—NH— or —NH—C(O)—O— and "sterol" can be a cholesterol attached via its C3 atom.

The following Table 1 provides calculated or database values for the pK of the imino containing moieties (I1) through to (I113). For quarternized imine moieties, a hypothetical value of 99 was introduced to merely highlight this fact.

TABLE 1 pK values for the moieties I1-I113

| moiety | imino | amino | ring N | guanido N |
|---|---|---|---|---|
| I1 | 10.49 | | | |
| I2 | 7.23 | | | |
| I3 | 7.23 | | | |
| I4 | 7.08 | | | |
| I5 | 8.41 | | | |
| I6 | 8.06 | | | |
| I7 | 7.87 | | | |
| I8 | 7.52 | | | |
| I9 | 11.58 | | | |
| I10 | 6.18 | | | |
| I11 | 6.61 | | | |
| I12 | 7.01 | | | |
| I13 | n.d. | | | |
| I14 | n.d. | | | |
| I15 | 5.62 | | | |
| I16 | 5.89 | | | |
| I17 | 0.63 | | | |
| I18 | 4.53 | | | |
| I19 | 6.22 | | | |
| I20 | 6.99 | | | |
| I21 | 5.36 | | | |
| I22 | 5.11 | | | |
| I23 | 5.85 | | | |
| I24 | 6.03 | | | |
| I25 | 12.06 | −5 | | |
| I26 | 12.37 | −4.91 | | |
| I27 | 12.37 | −4.91 | | |
| I28 | 12.37 | −4.91 | | |
| I29 | 12.37 | −3.58 | | |
| I30 | 12.3 | −3.68 | | |
| I31 | 12.37 | −3.58 | | |
| I32 | 12.06 | −5 | | |
| I33 | 12.68 | −3.49 | | |
| I34 | 12.66 | −3.58 | | |
| I35 | 10.98 | −5.43 | | |
| I36 | 12.98 | −4.25 | | |
| I37 | 12.52 | −3.12 | | |
| I38 | 12.82 | −4.01 | | |
| I39 | 13.13 | −3.93 | | |
| I40 | 13.12 | −3.68 | | |
| I41 | 12.37 | −3.25 | | |
| I42 | 12.68 | −4.04 | | |
| I43 | 12.99 | −3.06 | | |
| I44 | 12.98 | −3.71 | | |
| I45 | 9.1 | −4.89 | | |
| I46 | 9.37 | −3.47 | | |
| I47 | 10.66 | −3.56 | | |
| I48 | 99 | −3.47 | | |
| I49 | 8.47 | −4.89 | | |
| I50 | 9.02 | −3.47 | | |
| I51 | 10.31 | −3.56 | | |
| I52 | 99 | −3.47 | | |
| I53 | 7.73 | | | |
| I54 | 10.62 | −6.91 | | |
| I55 | 1.92 | | −5.58 | |
| I56 | 10.63 | −6.87 | | |
| I57 | 8.62 | | −7.89 | |
| I58 | 11.03 | −5.39 | | |
| I59 | 9.31 | | −4.75 | |
| I60 | 8.67 | −6.83 | | |
| I61 | 9.37 | −3.47 | | |
| I62 | 10.66 | −3.56 | | |
| I63 | 99 | −3.47 | | |
| I64 | 7.19 | −7.59 | | |
| I65 | 7.41 | −2.85 | | |
| I66 | 8.37 | −2.58 | | |
| I67 | 99 | −2.7 | | |
| I68 | 13.72 | | | −1.04 |
| I69 | 14.03 | | | 2.05 |
| I70 | 14.14 | | | 1.71 |
| I71 | 11.11 | | | 0.94 |
| I72 | 14.33 | | | 1.68 |
| I73 | 14.25 | | | −0.71 |
| I74 | 14.73 | | | −0.4 |
| I75 | 13.9 | | | −0.0 |
| I76 | 14.04 | | | −0.1 |
| I77 | 14.18 | | | −0.72 |
| I78 | 14.67 | | | −0.41 |
| I79 | 14.18 | | | −0.2 |
| I80 | 14.33 | | | −0.2 |
| I81 | 9.85 | | | −1.92 |
| I82 | 10.17 | | | −0.57 |
| I83 | 11.41 | | | −0.65 |
| I84 | 99 | −0.57 | | −13.15 |
| I85 | 14.33 | | | −0.98 |
| I86 | 14.33 | | | −0.57 |
| I87 | 14.47 | | | −0.68 |
| I88 | 99 | −0.57 | | −11.28 |
| I89 | 10 | −8.4 | | |
| I90 | 8.69 | −9.2 | | |
| I91 | 10.93 | −7.8 | | |

TABLE 1-continued pK values for the moieties I1-I113

| moiety | imino | amino | ring N | guanido N |
|---|---|---|---|---|
| I92 | 10.08 | −6.76 | | |
| I93 | 10.32 | −6.88 | | |
| I94 | 3.51 | | | |
| I95 | 3.51 | | | |
| I100 | 8.98 | −8.16 | | |
| I101 | 8.85 | −8.94 | | |
| I102 | 9.9 | −7.55 | | |
| I103 | 9.69 | −6.76 | | |
| I104 | 9.29 | −6.88 | | |
| I105 | 8.82 | −9.73 | | |
| I106 | 10.58 | −8.09 | | |
| I107 | 12.49 | −3.67 | | |
| I108 | 12.49 | −3.67 | | |
| I109 | 12.36 | −3.67 | | |
| I110 | 12.8 | −3.58 | | |
| I111 | 12.78 | −3.58 | | |
| I112 | 10.62 | −3.58 | | |
| I113 | 10.27 | −3.58 | | |

It becomes apparent from the data presented here, that most of the structures I1-I113 comprise preferred imino moieties having a pK greater 7.5 or even greater than 8.5.

The pK values can be taken from public databases. Alternatively, there is expert software in the public domain that can calculate, predict or extrapolate such values, e.g., ACD/Labs v7 (by Advanced Chemistry Development, Ontario, Canada) or the like.

The imino moieties analyzed above are illustrating the teachings of this invention, without limiting it to the specific examples. It is of course possible to change the position of substituents, in particular when ring systems such as pyrrols or pyridins are used for practicing this invention. It is also possible to replace the aliphatic radicals used throughout I1-I113 with aromatic residues or aryl moieties. The following list of compounds (A1) through to (A21) provides a few examples that should further illustrate such modifications, wherein L is defined as above.

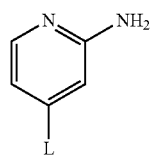 (A1)

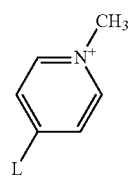 (A2)

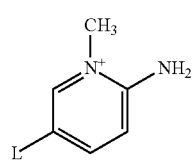 (A3)

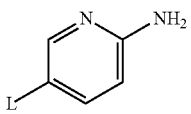 (A4)

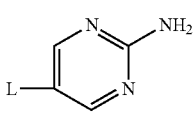 (A5)

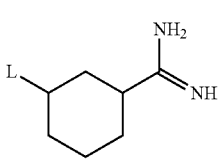 (A6)

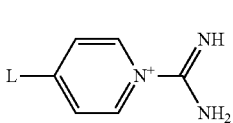 (A7)

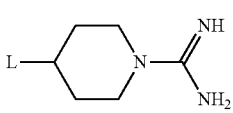 (A8)

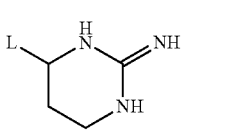 (A9)

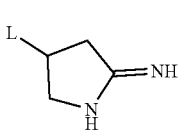 (A10)

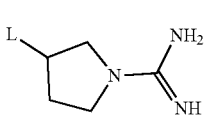 (A11)

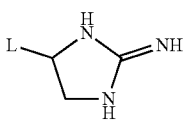 (A12)

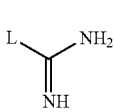 (A13)

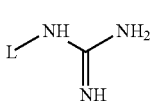 (A14)

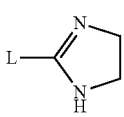 (A15)

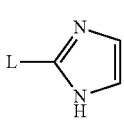 (A16)

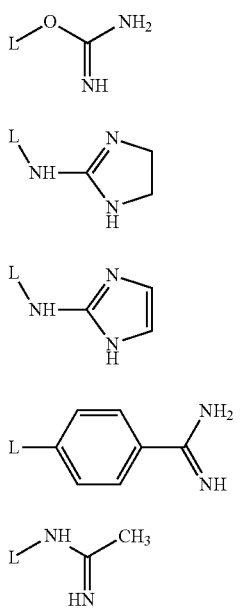

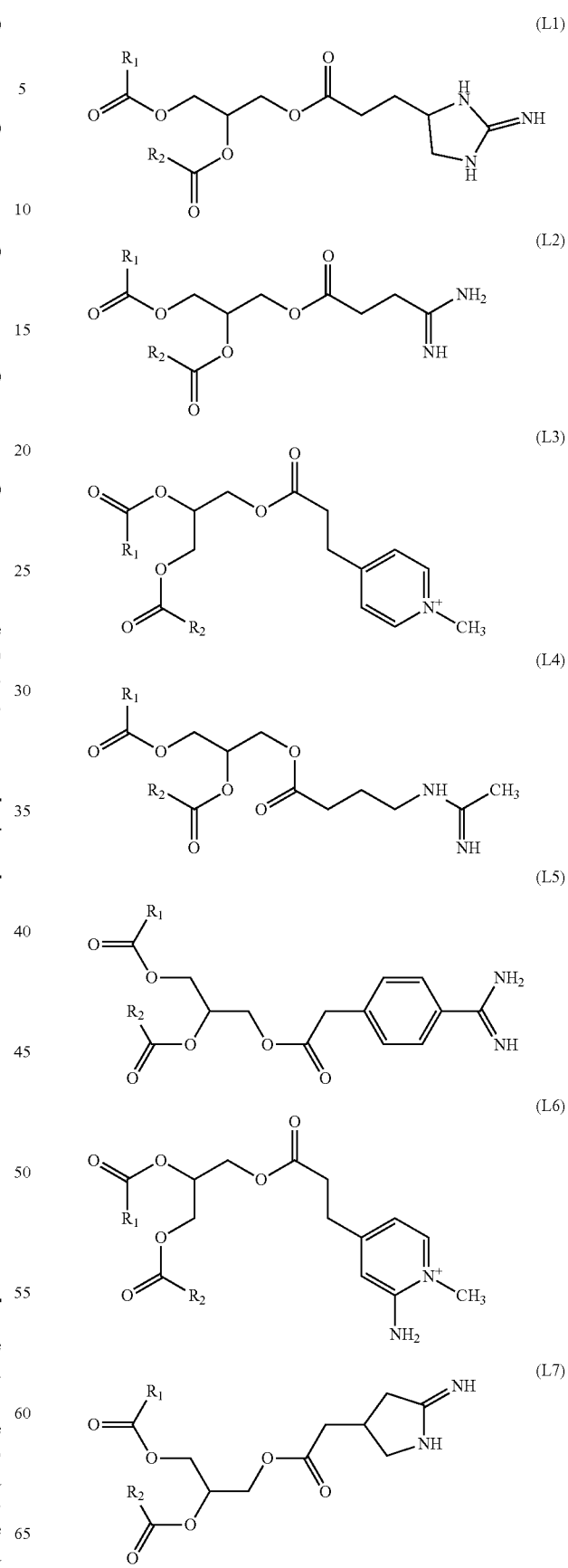

The following Table 2 provides calculated or database values for the pK of the imino containing moieties (A1) through to (A21)). For quarternized imino moieties, a hypothetical value of 99 was introduced to merely highlight this fact.

TABLE 2 pK values for structures (A1) to (A21).

| structure | atom | pK | atom | PK | atom | pK |
|---|---|---|---|---|---|---|
| A1 | ring | 7.29 | out | −7.16 | | |
| A2 | ring | 99 | | | | |
| A3 | ring | 99 | out | −6.76 | | |
| A4 | ring | 7.06 | out | −6.91 | | |
| A5 | ring | 4.74 | | | | |
| A6 | imino | 12.15 | amidin | −4.95 | | |
| A7 | imino | 3.07 | amidin | −12.14 | ring | 99 |
| A8 | imino | 14.24 | | | ring | −1.31 |
| A9 | imino | 14.18 | amidin | −0.72 | | |
| A10 | imino | 12.52 | amidin | −3.12 | | |
| A11 | imino | 14.18 | | | ring | −1.27 |
| A12 | imino | 14.25 | amidin | −0.71 | | |
| A13 | imino | 12.31 | amidin | −5 | | |
| A14 | imino | 13.75 | amidin | −0.76 | | |
| A15 | imino | 10.98 | amidin | −5.43 | | |
| A16 | imino | 7.96 | | | | |
| A17 | imino | 9.44 | amidin | −8.39 | | |
| A18 | imino | 9.78 | amidin | 0.95 | | |
| A19 | imino | 8.52 | out | −1.86 | | |
| A20 | imino | 11.97 | amidin | −6.3 | | |
| A21 | imino | 12.5 | amidin | −3.6 | | |

Again, many of the structures presented in the above Table 2 comprise preferred imino moieties having a pK greater 7.5 or even greater than 8.5, As mentioned above, the charged imino moieties can be combined with lipid anchors or hydrophobic portions to yield lipids or amphiphiles that are capable of forming lipid bilayers by themselves or can be integrated into lipid membranes formed from other lipids or amphiphiles, in some embodiments, specific lipids or amphiphiles are selected from the examples L1 to L17 presented below, -continued (L8) 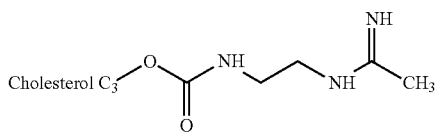

(L9) 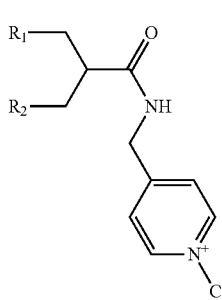

(L10) 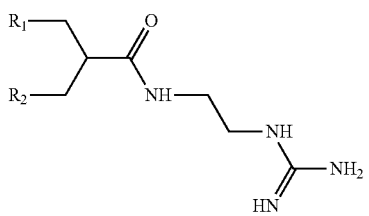

(L11) 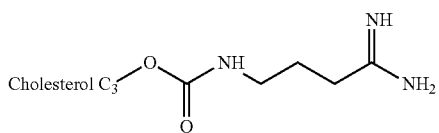

(L12) 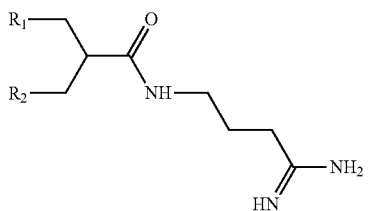

(L13) 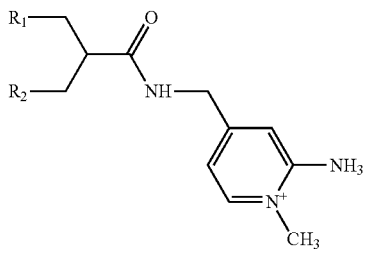

(L14) 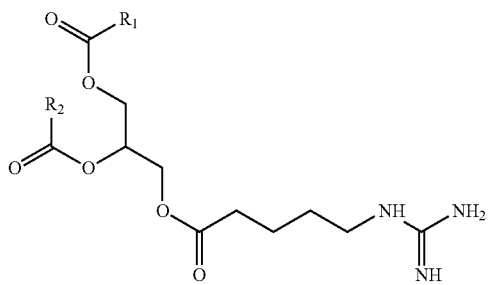

-continued (L15) 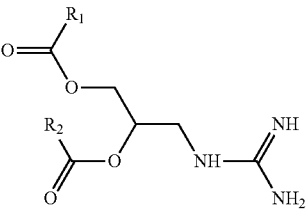

(L16) 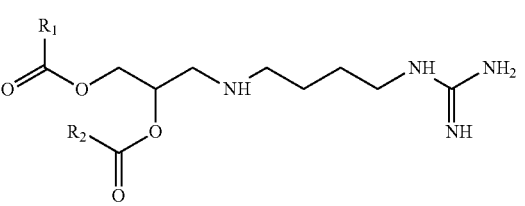

(L17) 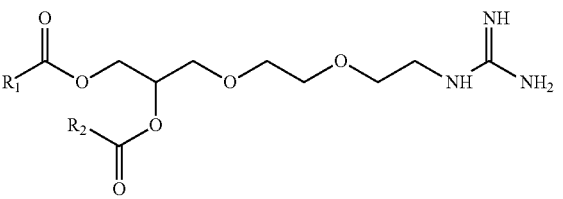

wherein $R_1$ and $R_2$ are independently from each other an alkyl, alkenyl or alkinyl moieties having between 8 and 21 carbon atoms and 0, 1 or 2 unsaturated bonds.

Some of these lipids have been presented earlier in the literature, for example the guanido lipids in WO91116024, WO97/43363, WO98105678, WO01/55098, WO2008/137758 (amino acid lipids), in EP 0685234 (based on diacylglycerols), U.S. Pat. No. 5,965,434 (also based on diacylglycerols) or the pyridinium compounds in U.S. Pat. No. 6,726,894. Furthermore, as demonstrated in WO29086558 or iluustrated in structure (15), it is also possible to use alternative lipid backbones, e.g. those comprising a dioxolane linker segment while maintaining the functionality of the respective head groups.

Lipid Mixtures and Optional Other Lipids

The present invention discloses lipid mixtures comprising anionic and cationic amphiphiles; wherein at least a portion of the cationic amphiphiles are imino lipids that are substantially charged under physiological conditions, and wherein further at least a portion of the anionic amphiphiles are carboxyl lipids or phosphate lipids.

A co-presence of both cationic lipids comprising a charged imino moiety in their polar head group and anionic lipids comprising a carboxyl or phosphate function in their polar head group is a central feature of this invention. That is, liposomes or lipid assemblies that substantially lack one of these elements are not contemplated in the practice of the present invention. The cationic imino lipids and the anionic lipids can be present in different ratios; said ratios are characterized herein as "charge ratios" (cation:anion ratios, C/A, see definitions) throughout this disclosure. In many embodiments the C/A ratio is above 0.33, in preferred embodiments this ratio is above 0.5 and in some embodiments the ratio is equal or above 0.66. In preferred aspects of said embodiments the C/A is equal or below 3, in further preferred aspects the ratio is equal or below 2 and in particularly preferred aspects the ratio is equal or below 1.5.

In many aspects of said embodiments, the resulting lipid mixture has amphoteric character. Imino lipids having a pK of more than 7.5, and even more so the preferred imino lipids having a pK of 8.5 or higher are essentially charged under physiological conditions, their actual charge becomes close and eventually identical with their nominal charge. The typical pK of carboxyl lipids is between 4.5 and 6 and these lipids are therefore also charged at physiological pH. Mixtures of both the imino and the carboxyl lipid therefore have net negative charge at physiological pH whenever C/A is smaller than 1, the net charge become 0 at C/A=1 and positive for C/A>1.

At low pH; the anionic charge disappears around the pK of the carboxyl lipid, which renders lipid mixtures having a C/A<1 first neutral and then positively charged. The charge reversal is characteristic for C/A<1 and defines the amphoteric character. Lipid mixtures having C/A=1 or C/A>1 also undergo a reduction of negative charges at low pH, but no charge reversal. It should however be noted, that the relationship between C/A and amphoteric character of the resulting lipid assemblies implies a statistic, essentially equal distribution of the charged moieties across a given bilayer. That means that the inner and outer leaflet of a membrane must have the same composition of charged lipids to maintain the full validity of these calculations. This may not always be the case as demonstrated in example 9 and liposomes of amphoteric character can be formed even with lipid mixtures having C/A>1. Still, the correlations between membrane composition and amphoteric character disclosed here give good guidance for the selection of lipid mixtures.

The lipid mixtures may further comprise additional cationic, anionic, neutral/zwitterionic, or functionalized lipids. Additional cationic lipids may be known components such as DOTAP, DODAP, DC-Chol and the like. Additional anionic lipids may be selected from negatively charged phospholipids, such as phosphatidylglycerol, phosphatidic acid, dicetylphosphoric acid, cardiolipin and the like. Neutral or zwitterionic lipids are cholesterol, phosphatidylethanolamine, phosphatidylcholine, sphingomyelin and the like.

In preferred embodiments the neutral lipid is cholesterol. Further preferred are variants wherein the lipid mixtures comprise between 10 mol % and 50 mol % of cholesterol, even more preferred are variants with about 20 mol % and 40 mol % cholesterol.

An important group of functionalized lipids are those comprising polymer extensions such polyethylenglycol (PEG-lipids). Numerous PEGylated lipids are known in the state of the art and essential differences can be found in (i) the size and degree of branching of the PEG-chain, (ii) the type of the linker group between PEG and the membrane-inserted portion of the molecule and (iii) the size of the hydrophobic, membrane inserted domain of a PEGylated lipid. Further aspects of PEGylation are (iv) the density of the modification in the lipid assemblies and (v) their orientation within such lipid assemblies.

In many embodiments of the aspect (i), the PEG fragment has a molecular weight between 500 Da and 5,000 Da, in more preferred embodiments, this fragment has a molecular weight of about 700 Da to 2,500 Da and even more preferred are PEG fragments of about 2,000 Da. In many such embodiments, the PEG moiety is a single chain, non-branched PEG.

Typical embodiments of aspect (ii) are phosphoethanolamine moieties, diacylglycerols moieties or the polar head groups of ceramides.

The size of the hydrophobic, membrane inserted domain characterized in aspect (iii) is a further important feature of such molecules as it determines the membrane residence time of the PEG lipid within a bilayer. As an example, PEGylated lipids having a short hydrophobic domain such as DMPE-PEG2000 dimyristoylphosphatidylethanolamine-PEG conjugate, wherein the PEG chain has a molecular weight of 2000 Da) diffuse from a given membrane within seconds, whereas the DSPE-PEG2000 homologue resides in a bilayer for many hours or days (see Silvius, J. R. and Zuckermann, M. J. (1993) Biochemistry 32, 3153-3161 or Webb, M. S. et al (1998) in Biochim Biophys Acta 1372: 272-282 or Wheeler et al. (1999) in Gene Ther 6: 271-281.

PEGylation at the same time provides colloidal stability to liposomes, in particular to combinations of cationic liposomes with anionic nucleic acid cargoes as illustrated in U.S. Pat. No. 6,287,591 but also impairs the cellular uptake and/or endosomal of liposomes (see Shi, F. et al. (2002) in Biochem. J. 366:333-341). A transient PEGylation is now state of the art and satisfies the need for both colloidal stability and activity of the particles.

A further aspect (iv) of PEGylation is the density of such modification, which should be between 0.5 and 10 mol % of the lipid mixture, in preferred embodiments the degree of PEGylation is about 1 to 4 mol %.

Since PEGylation of a given bilayer stabilizes the lamellar phase of the lipid assembly and impairs lipid fusion associated with the formation of a hexagonal phase, the amount of residual PEG moieties in a bilayer must be minimal. This can be achieved by titration of the required amounts of PEGlipids. In some embodiments of aspect (v) the liposomes are thus PEGylated on both membrane leaflets and the amount of PEG is minimized. In another variant, PEG removal is as complete as possible. While this is easily achieved for the PEG lipids associated with the outer bilayer, diffusion is essentially not possible for PEG lipids attached to the interior of the lipid structure. It is thus a preferred embodiment of the aspect (v) of this invention to provide liposomes comprising charged imino and carboxyl or phosphate lipids further comprising PEGylated lipids, wherein said PEGylated lipids are essentially situated on the outer surface.

Such liposomes can be characterized by the process of their production, wherein liposomes are formed in a first step and this step also comprises encapsulation of cargo molecules. The PEG-lipids are then inserted into the outer bilayer of the pre-fabricated liposomes in a second step e.g. by addition of a micellar solution of PEGylated lipids to the liposome suspension. In a specific embodiment of such process, the liposomes sequestering nucleic acids are formed by mixing of a watery solution of nucleic acids with an alcoholic solution of lipids. Liposomes entrapping nucleic acids are formed spontaneously and the PEGylated lipids are added in a subsequent step.

With particular advantage, such process can be practiced with amphoteric liposomes, as these liposomes already provide colloidal stability and the time element between liposome formation and PEGylation is less critical. The preparation of amphoteric liposomes encapsulating nucleic acids is disclosed in WO 02/056012, its continuation US2007/0252295 or further in WO 07/107304.

In a preferred embodiment, amphoteric liposomes comprising imino and carboxyl or phosphate lipids are PEGylated on their outer surface by providing the required amounts of PEG lipid together with the neutralization buffer. For that, the PEG lipids can be dissolved in the neutralization buffer. In another embodiment, said liposomes are formed and neutralized and the PEG lipid is added separately after a time interval of between 0.1 s and several days. In yet another embodiment, the liposomes are formed and neutralized and the liposome suspension is further concentrated and the PEG lipids are added after the concentration of the materials. In yet another embodiment, the liposomes are formed and neutralized and concentrated and the non-encapsulated nucleic acid is removed and optionally the buffer for the liposome suspension is exchanged and the PEG lipids are added afterwards. In summary, the PEG lipids can be added at any time after the formation and closure of the liposomes.

In other embodiments the liposomes comprising imino and carboxyl or phosphate lipids have pH-sensitive cationic character and are PEGylated on their outer surface by providing the required amounts of PEG lipid upon formation and closure of said liposomes, following the steps outline above. Since pH-sensitive liposomes are more prone to form aggregates in the presence of nucleic acids, a rapid PEGylation is preferred and the PEG lipids are added immediately upon closure of the liposomes, e.g. between 0.1 s and 1 min after their production.

In contrast to the above methods yielding product liposomes that are essentially PEGylated on their outer surface, presence of PEGylated lipids during the actual formation of liposomes; that is before the nascent structures close, results in a different product. Although structural data have not yet been obtained, the skilled artisan would expect in such situation that a substantial amount of PEG moieties also resides in the inner leaflet of the membrane. This is similar to the situation of the nucleic acid cargo which also has access to both leaflet of the nascent liposome and of which a substantial portion can be detected inside the liposomes, once these have closed.

Lipid Assemblies

The components mentioned herein can be assembled in various structures known to the skilled artisan. These can be liposomes comprising one or a number of individual bilayers, other supramolecular lipid assemblies or vesicles having a sizeable interior volume that provides an aqueous phase. It also can be emulsion droplets or structures in the form of lipoplex assemblies, the latter in many embodiments comprising electrostatic complexes between the lipids and nucleic acids. In preferred embodiments, these structures are liposomes or vesicles. In many embodiments, the liposomes or vesicles have a sizeable aqueous interior. In many aspects of this invention, an active pharmaceutical ingredient is complexated, encapsulated, sequestered or otherwise associated with the lipid assemblies.

Given the large number of useful imino and carboxyl or phosphate and additional lipids, a very high number of potentially useful combinations does exist, thereby creating a further need for selection and optimization amongst the many variants. WO08/043575 gives specific guidance and provides a method for the optimization of complex lipid assemblies, specifically for lipid bilayers, as discussed in further detail herein. In brief, the teachings in WO08/043575 demonstrate that amphoteric lipid mixtures form stable bilayers both under acidic and neutral pH conditions, however, the bilayers formed from these lipid mixtures can undergo phase transition and fusion at their isoelectric point, which typically is at slightly acidic conditions. WO08/043575 discloses the use of moderately sized or small lipid head groups for the charged lipid components. WO 08/043575 also teaches the use of large or bulky buffer ions to stabilize the lamellar phases at low pH during the loading procedure, as well as the use of large or bulky buffer ions to stabilize the lamellar phases at neutral pH during storage. In particular, reference is made to pages 44-57 of WO 08/043575, which feature the essential elements cited above. The reference further discloses the use of neutral lipids bearing a small head group such to maximize the fusion activity. Typical neutral lipids for improved fusion are cholesterol or DOPE. Specific considerations and optimization rules for the neutral lipids are further presented in WO 09/047006, in particular on pages 63 through to 70.

Altogether, WO 08/043575 or WO 09/047006, together referred to as "the References" herein provide rational guidance for the optimization of lipid assemblies. The References are not restricted to amphoteric: liposomes, but provide a comprehensive model for the structure-activity relationship of lipid assemblies.

The present invention represents an advance in the art, as it provides optimized methods of formulating liposomes that are capable of circumventing cellular binding, interaction or competition with lipoproteins or other serum components. While the methods taught by References provide the information for the necessary fusogenicity of lipid assemblies, they are silent with respect to a prediction of the cellular binding of the liposomes.

Thus, it is an object of the present invention to provide lipid assemblies, lipid mixtures, and liposomes formulated by the method disclosed in the References in combination with the unexpected properties observed when using an imino lipid that is substantially charged under physiological conditions is used in combination with an anionic lipid having a carboxyl or phosphate, that is, negatively charged moiety. Without wishing to be bound by theory, the novel compositions formulated herein can better facilitate lipoprotein-like cellular binding and uptake—a feature that is not known in the art.

The lipid mixtures described herein can have amphoteric or pH-sensitive cationic properties, both of which are generally conveyed towards the lipid assemblies or liposomes by the lipids forming them. Charge properties can easily predicted as described in WO 02/066012 for a symmetrical distribution of the lipids towards both leaflets of a lipid membrane or bilayer. However, in some cases the lipid distribution of the outermost leaflet may differ from other parts of the assembly. Macroscopically, lipid mixtures comprising charged imino lipids in combination with carboxyl or phosphate lipids having C/A somewhat larger than 1 may therefore still form liposomes having amphoteric character, as demonstrated in example 9 and FIG. 1

For purposes of in silico optimization and prediction, lipid mixtures of the present invention having a C/A<1 are considered amphoteric and can form lipid assemblies categorized as "amphoter I" mixtures according to the classification of the References. In other embodiments, lipid mixtures are used that have C/A=1 or C/A>1; these are pH-sensitive cationic lipid mixtures; that is their charge is neutral or cationic at physiological pH and becomes more cationic with descending pH. The pH-sensitive cationic mixtures of said embodiments do no longer have an isoelectric point as it is the case with their amphoteric counterparts. Still, the structure-activity relationships provided in the References are applicable as these provide a universal understanding of the phase behaviour of lipid assemblies in combination with solute and ions irrespective of their charge.

For the sake of clarity, lipid mixtures of the present invention comprise one or more cationic lipids having an imino group that is substantially charged at physiological pH, further comprising one or more anionic lipids having a carboxyl or phosphate group, optionally further comprising neutral lipids.

The amphoteric character of liposomes has further advantages. The negative surface charge of such liposomes or lipid assemblies improves greatly the colloidal stability of the liposomes in suspension. This is of particular importance in combinations with polyanionic cargoes such as nucleic acids, which easily produce aggregates with cationic liposomes.

The negative to neutral surface charge of the amphoteric lipid assemblies or liposomes is also advantageous when administering the liposomes in vivo, where it prevents unspecific adsorption on endothelia or the formation of aggregates with serum components as observed with cationic liposomes (see Santel et al., (2006) in Gene Therapy 13: 1222-1234 for endothelial adsorption of cationic liposomes or Andreakos et al., (2009) in Arthritis and Rheumatism, 60:994-1005 for the prevention of aggregate formation with amphoteric liposomes).

Thus; in preferred embodiments, the liposomes of this invention have amphoteric character Within this group, it is of advantage to avoid very low percentages of the cationic component to maintain effective loading of the particles with polyanionic cargos, e.g. nucleic acids. In further preferred embodiments, the C/A is greater 0.5.

When applied systemically, that is, into the bloodstream, the liposomes undergo a certain distribution within the body. Typical target sites are liver and spleen, but also include the circulating phagocytic cells. The liposomes also contact the endothelia surrounding the blood vessels and may transfect these cells. The accumulation of liposornes in inflamed sites and tumors is of particular therapeutic relevance.

The skilled artisan would be aware of methods to direct the distribution of particles towards one or the other site. It is well known that liposomes having a small diameter of about 150 nm or less can penetrate the liver endothelium, thus gaining access to the hepatocytes and other cells of the liver parenchyma. In aspects where targeting of the liver hepatocytes is of therapeutic interest, the liposomes of this inventions can be 150 nm or less in diameter, in preferred embodiments, the liposomes can be less than 120 nm in diameter.

It is also well known that particles having a diameter of 100 nm or more are well recognized by phagocytic cells. Therefore, in embodiments where macrophages or dendritic cells constitute the target of interest, the liposomes of this invention are 120 nm or larger. In some embodiments, these liposomes are 150 nm or larger. In other embodiments these liposomes can be as a large as 250 nm, or up to 400 nm in size.

It has also been described that surface charge may influence the circulation time, hence the biodistribution of liposomes and it is well established that PEGylation reduces the surface charge and results in prolonged circulation of the liposomes. Prolonged circulation is generally thought to maximize the distribution towards tumors. Therefore, in aspects where tumors constitute the target of interest, the liposomes of this invention have a small net surface charge and are characterized by a C/A of between 0.67 end 1.5. In preferred embodiments for such applications the lipid mixtures forming said liposomes have a C/A between 0.8 and 1.25. Also, the liposomes targeting tumors are of small size. In preferred embodiments such liposomes are smaller than 150 nm, in further preferred embodiments the liposomes are smaller than 120 nm. In some embodiments, the liposomes further comprise PEG lipids.

Cargoes for the Liposomes of this Invention

The liposomes or lipid assemblies of this invention can sequester or encapsulate at least one active agent. Said active agent may comprise a drug. In some embodiments, said active agent may comprise one or more nucleic acids. In preferred embodiments, the active ingredient consists of nucleic acids.

Without being limited to such use, the liposornes or lipid assemblies described in the present invention are well suited for use as carriers for nucleic acid-based drugs, such as for example, oligonucleotides, polynucleotides and DNA plasmids. These drugs are classified into nucleic acids that encode one or more specific sequences for proteins, polypeptides or RNAs and into oligonucleotides that can specifically regulate protein expression levels or affect the protein structure through, inter alia, interference with splicing and artificial truncation.

In some embodiments of the present invention, therefore, the nucleic acid-based therapeutic may comprise a nucleic acid that is capable of being transcribed in a vertebrate cell into one or more RNAs, which RNAs may be mRNAs, shRNAs, miRNAs or ribozymes, wherein such mRNAs code for one or more proteins or polypeptides. Such nucleic acid therapeutics may be circular DNA plasmids, linear DNA constructs, like MIDGE vectors (Minimalistic Immunogenically Defined Gene Expression) as disclosed in WO 98121322 or DE 19753182, or mRNAs ready for translation (e.g., EP 1392341).

In other embodiments of the invention, oligonucleotides may be used that can target existing intracellular nucleic acids or proteins. Said nucleic acids may code for a specific gene, such that said oligonucleotide is adapted to attenuate or modulate transcription, modify the processing of the transcript or otherwise interfere with the expression of the protein. The term "target nucleic acid" encompasses DNA encoding a specific gene, as well as all RNAs derived from such DNA, being pre-mRNA or mRNA. A specific hybridisation between the target nucleic acid and one or more oligonucleotides directed against such sequences may result in an inhibition or modulation of protein expression. To achieve such specific targeting, the oligonucleotide should suitably comprise a continuous stretch of nucleotides that is substantially complementary to the sequence of the target nucleic acid.

Oligonucleotides fulfilling the abovementioned criteria may be built with a number of different chemistries and topologies. The oligonucleotides may comprise naturally occurring or modified nucleosides comprising, but not limited to, DNA, RNA, locked nucleic acids (WA's), unlocked nucleic acids (UNA's), 2'O-methyl RNA (2'Ome), 2' O-methoxyethyl RNA (2'MOE) in their phosphate or phosphothioate forms or Morpholinos or peptide nucleic acids (PNA's). Oligonucleotides may be single stranded or double stranded.

Oligonucleotides are polyanionic structures having 8-60 charges. In most cases, these structures are polymers comprising nucleotides. The present invention is not limited to a particular mechanism of action of the oligonucleotides and an understanding of the mechanism is not necessary to practice the present invention. The mechanisms of action of oligonucleotides may vary and might comprise inter alia effects on splicing, transcription, nuclear-cytoplasmic transport and translation.

In a preferred embodiment of the invention, single stranded oligonucleotides may be used, including, but not limited to DNA-based oligonucleotides, locked nucleic acids, 2'-modified oligonucleotides and others, commonly known as antisense oligonucleotides. Backbone or base or sugar modifications may include, but are not limited to. Phosphothioate DNA (PTO), 2'O-methyl RNA (2'Ome), 2'Fluoro RNA (2'F), 2' O-methoxyethyl-RNA (MOE), peptide nucleic acids (PNA), N3'—P5' phosphoamidates (NP), 2'fluoroarabino nucleic acids (FANA), locked nucleic acids (LNA), unlocked nucleic acids (UNA), Morpholine phosphoamidate (Morpholino), Cyclohexene nucleic acid (CeNA), tricyclo-DNA (tcDNA) and others. Moreover, mixed chemistries are known in the art, being constructed from more than a single nucleotide species as copolymers, block-copolymers or gapmers or in other arrangements.

In addition to the aforementioned oligonucleotides, protein expression can also be inhibited using double stranded RNA molecules containing the complementary sequence motifs. Such RNA molecules are known as siRNA molecules in the art (e.g., WO 99/32619 or WO 02/055693). Other siRNAs comprise single stranded siRNAs or double stranded siRNAs having one non-continuous strand. Again, various chemistries were adapted to this class of oligonucleotides. Also, DNA I RNA hybrid systems are known in the art. Other varieties of siRNA's comprise three-stranded constructs wherein two smaller strand hydridize to one common longer strand, the so-called meroduplex sisiRNA's having nicks or gaps in their architecture.

In another embodiment of the present invention, decoy oligonucleotides can be used. These double stranded DNA molecules and chemical modifications thereof do not target nucleic acids but transcription factors. This means that decoy oligonucleotides bind sequence-specific DNA-binding proteins and interfere with the transcription (e.g., Cho-Chung, et al., in Curr. Opin. Mol. Ther., 1999).

In a further embodiment of the invention, oligonucleotides that may influence transcription by hybridizing under physiological conditions to the promoter region of a gene may be used. Again, various chemistries may adapt to this class of oligonucleotides.

In a still further alternative of the invention, DNAzymes may be used. DNAzymes are single-stranded oligonucleotides and chemical modifications thereof with enzymatic activity. Typical DNAzymes, known as the "10-23" model, are capable of cleaving single-stranded RNA at specific sites under physiological conditions. The 10-23 model of DNAzymes has a catalytic domain of 15 highly conserved deoxyribonucleotides, flanked by 2 substrate-recognition domains complementary to a target sequence on the RNA. Cleavage of the target mRNAs may result in their destruction and the DNAzymes recycle and cleave multiple substrates.

In yet another embodiment of the invention, ribozymes can be used. Ribozymes are single-stranded oligoribonucleotides and chemical modifications thereof with enzymatic activity. They can be operationally divided into two components, a conserved stem-loop structure forming the catalytic core and flanking sequences which are reverse complementary to sequences surrounding the target site in a given RNA transcript. Flanking sequences may confer specificity and may generally constitute 14-16 nt in total, extending on both sides of the target site selected.

In other embodiments of the invention, aptamers may be used to target proteins. Aptamers are macromolecules composed of nucleic acids, such as RNA or DNA, and chemical modifications thereof that bind tightly to a specific molecular target and are typically 15-60 nt long. The chain of nucleotides may form intramolecular interactions that fold the molecule into a complex three-dimensional shape. The shape of the aptamer allows it to bind tightly against the surface of its target molecule including but not limited to acidic proteins, basic proteins, membrane proteins, transcription factors and enzymes. Binding of aptamer molecules may influence the function of a target molecule.

All of the above-mentioned oligonucleotides may vary in length between as little as 5 or 10, preferably 15 and even more preferably 18, and as many as 50 or 60, preferably 30 and more preferably 25, nucleotides per strand. More specifically, the oligonucleotides may be antisense oligonucleotides of 8 to 50 nucleotides length that catalyze RNAseH mediated degradation of their target sequence or block translation or re-direct splicing or act as antagomirs; they may be sIRNAs of 15 to 30 basepairs length; or they may further represent decoy oligonucleotides of 15 to 30 basepairs length. Alternatively, they can be complementary oligonucleotides influencing the transcription of genomic DNA of 15 to 30 nucleotides length; they might further represent DNAzymes of 25 to 50 nucleotides length or ribozymes of 25 to 50 nucleotides length or aptamers of 15 to 60 nucleotides length. Such subclasses of oligonucleotides are often functionally defined and can be identical or different or share some, but not all, features of their chemical nature or architecture without substantially affecting the teachings of this invention. The fit between the oligonucleotide and the target sequence is preferably perfect with each base of the oligonucleotide forming a base pair with its complementary base on the target nucleic acid over a continuous stretch of the abovementioned number of oligonucleotides. The pair of sequences may contain one or more mismatches within the said continuous stretch of base pairs, although this is less preferred. In general the type and chemical composition of such nucleic acids is of little impact for the performance of the inventive liposomes as vehicles be it in vivo or in vitro, and the skilled artisan may find other types of oligonucleotides or nucleic acids suitable for combination with the amphoteric liposomes of the invention.

In certain aspects and as demonstrated herein, the liposomes according to the present invention are useful to transfect cells in vitro, in vivo or ex vivo.

Specific Embodiments

Cholesterol Based Lipids

To illustrate the teachings of this invention, cationic derivatives of cholesterol comprising guanido moieties (charged imino group, CHOL-GUA), imidazol moieties (non-charged imino group, CHIM) or dimethylamino or trimethyl ammonium moieties (non-imino, but charged groups, DC-CHOL or TC-CHOL) were systematically combined with different anionic lipids.

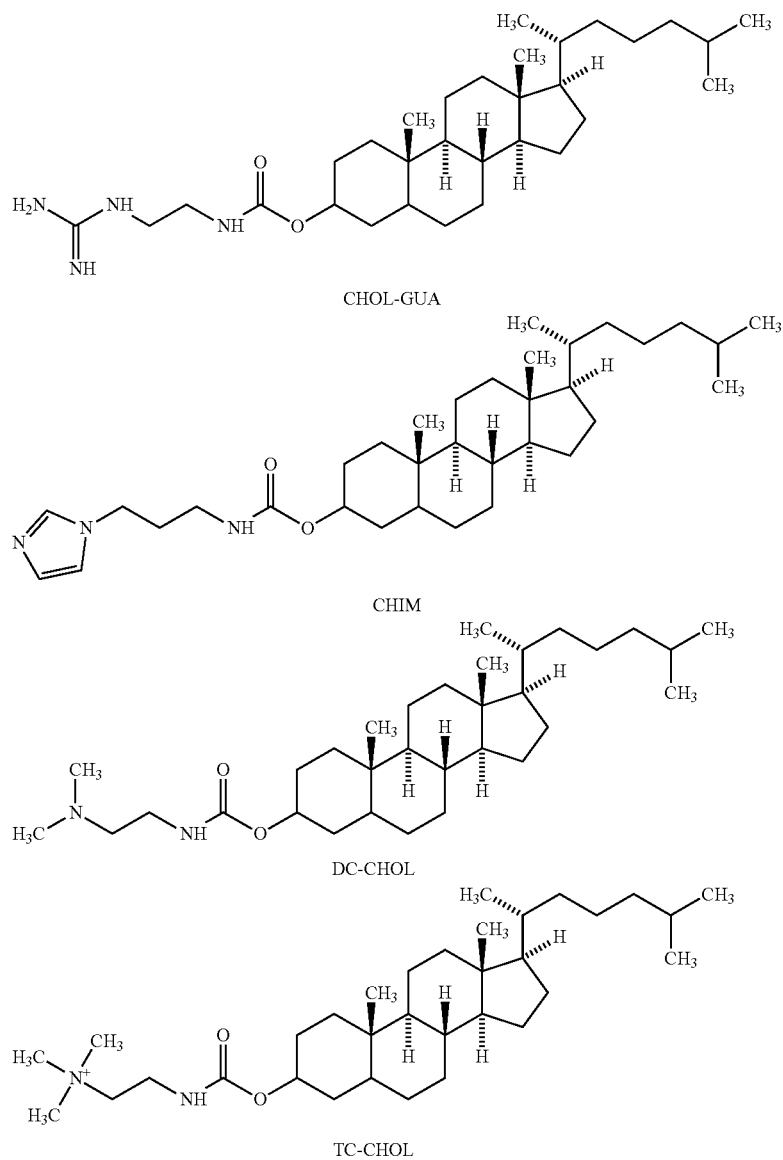

CHOL-GUA

CHIM

DC-CHOL

TC-CHOL

The anionic lipids used were CHEMS (cholesterol as hydrophobic portion, carboxylic acid charge group), DMGS or DOGS (diacylglycerols hydrophobic portion, carboxylic acid charge group) or DOPA (diacyl glycerol as hydrophobic portion, phosphate ester charge group). For most of the cation/anion combinations, a series of 8 binary mixtures having C/A ratios between 0.33 and 2 was prepared, combinations of the cationic lipids with DOPA were tested at C/A 0.75 and 1. Cholesterol was added to all lipid mixtures to constitute between 20 and 40 mol %, as indicated.

All liposomes were loaded with PLK-1 siRNA, an oligonucleotide capable of inhibiting the production of the cell cycle kinase PLK-1 and successful transfection was measured by inhibition of cell viability of the test cells (see also Haupenthai et al., int. J. Cancer (2007), 121:206-210. Unspecific inhibition of the cell viability, that is, cytotoxic effects, were monitored by control preparations comprising a non-targeting siRNA of the same general composition and in the same amounts.

The transfection of cells was followed in regular cell culture medium or with the additional presence of 10% mouse serum, a potent inhibitor of cellular uptake for many amphoteric liposomes. The efficacy of transfection is expressed as IC50, the concentration needed to achieve a 50% inhibition of the cell viability.

The ratio between the IC50 in regular medium and the IC50 upon addition of mouse serum is used as a metric for the inhibition of the cellular uptake by mouse serum. This ratio is 5 or higher for liposomes without specific targeting properties. It is 5 or lower for the liposomes of this invention; that is liposomes comprising charged imino groups in combination with negatively charged lipids.

As further demonstrated in examples 14, the best serum-resistant transfection of HeLa cells can be achieved by combinations of CHOLGUA with the carboxyl lipid DOGS. Particular good results were obtained in the presence of less than 40% cholesterol and for mixtures having a C/A of between 0.5 and 1.5. If all other components such as DOGS or cholesterol were kept constant and the GUA head group was exchanged against a dimethylamine as in DC-CHOL, the liposomes are still active in the absence, but no longer in the presence of mouse serum. The same can be observed for combinations of CHIM and DMGS.

Combinations of cholesterol-based cationic lipids with the phosphate lipid DOPA resemble the findings in that the best activities was observed for the imino lipid CHOLGUA. Also, serum-resistant transfection of CHOLGUA:DOPA liposomes could be observed, although with substantial inhibition compared to the absence of serum. Combinations for DOPA with CHIM or DC-CHOL did not result in any transfection in the presence of serum.

DACA-Based Lipids

To further investigate the dependence of the serum resistant transfection from head group chemistry, the following lipids were synthesized using a common dialkyl-carboxylic acid (DACA) anchor as their hydrophobic domain:

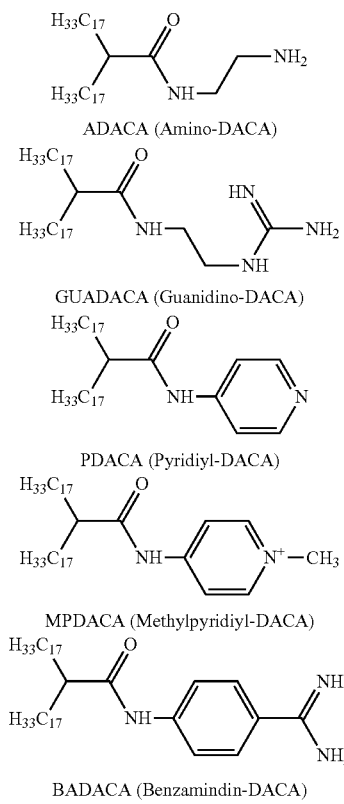

Wherein the DACA moiety was obtained by addition of oleyliodide to oleic acid as described in the example 10 and the resulting compound is:

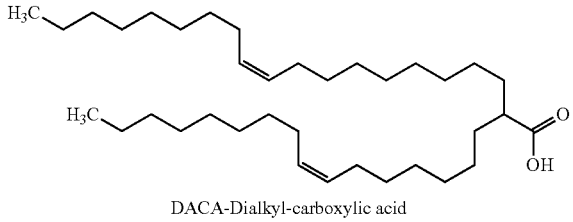 [SMILES: CCCCCCCC/C=C\CCCCCCCCC(CCCCCC/C=C\CCCCCCCC)C(=O)O]

DACA-Dialkyl-carboxylic acid

Out of the cationic lipids, GUADACA, MPDACA or BADACA have a charged imine moiety in their polar head groups. The head group of PDACA is essentially uncharged due to the low pK of the pyridine moiety (calculated pK is 5.9) while the methylated variant results in the formation of the constantly charged pyridinium compound MPDACA. ADACA has a high enough pK of about 9, but lacks the imine component. However, small amounts of the respective enamine may form from that component as the amino group is situated in 0-position from the amide, allowing mesomeric stabilization of the imine form.

Combinations with the anionic lipids CHEMS, DMGS, DOGS and DOPA were prepared as described above for the cholesterol based lipids and similar series of different liposomes having various C/A ratios of between 0.33 and 2 (or 0.75 and 1 for the phosphate lipid) were produced.

Also, the liposomes were loaded with siRNA targeting FLK-1 or an unrelated sequence and the transfection properties were tested on HeLa cells in the presence or absence of mouse serum.

As further demonstrated in examples 14 and 15, serum-resistant transfection of HeLa cells can be achieved by combinations of GUADACA or MPDACA with carboxyl lipids or phosphate lipids. In addition, these lipids yield very efficient transfection of PLK-1 siRNA also in the absence of serum. This implies that there is no activation of the liposomes with serum components as recently described for liposomes having a dirnethylamino head group (Akinc et al., Md. Ther. (2010) electronic publication on May 11th, ahead of print. DOI: 10.1038/mt.2010.85). Very high levels of carrier activity are also observed for C/A ratios between 0.5 and 1.5 for the combinations with the carboxylic lipids and for C/A 0.75 or 1 for the phosphate lipids. In many of these cases, formulations have amphoteric charge properties.

A lack of methylation of the pyridinium compound MPDACA gives the related PDACA. While still bearing an imine function, this function is no longer charged as in MPDACA; PDACA is also not active as a cationic lipid for transfection purposes. In yet another variant the aromatic ring of the head group was kept, but the charged imine was then presented as part of an extra-annular aminide group. This compound was found active as a lipid for transfection, e.g. in combinations with CHEMS or DMGS where it also resulted in serum-resistant transfection.

Additional Lipids Based on Dialkylcarboxylic Acids.

Similar findings have been made using the pyridinium lipid SAINT'-18 as described in U.S. Pat. No. 6,726,894 (structure 31).

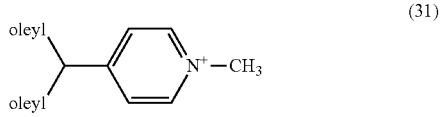

(31)

SAINT-18 was combined with various lipid anions, such as CHEMS. DMGS or DOGS. The ratios of the cationic and anionic lipids were varied in a systematic way and the resulting binary mixtures optionally were further supplied with 20 or 40 mol % cholesterol. The individual lipid mixtures were transformed into liposomes and used for the encapsulation of an active and control siRNA. When tested on HeLa cells in the presence of normal cell culture medium, efficient and specific inhibition of the cell viability was observed for numerous of the tested formulations, as demonstrated in Example 8. However, none of the liposomes having a C/A>=1 yielded transfection of cells in the presence of mouse serum. In stark contrast, a great many of the amphoteric formulations resisted the serum challenge and did transfect the cells effectively. Furthermore, the effect was specific to the PLK-1 siRNA and much higher concentrations of liposomes loaded with an unrelated siRNA (SCR) were needed to unspecifically inhibit cell proliferation. The best results were obtained by using SAINT18 in combination with DMGS. Liposomes comprising SAINT-18 and DMGS, further characterized by C/A<1 are therefore within the purview of this invention.

Amino Acid Based Lipids

To further illustrate the teachings of this invention, the cationic guanido lipid PONA (palmitoyl-oleoyl-nor-arginine, structure 21) was combined with various lipid anions such as CHEMS or DMGS. The ratios of the cationic and anionic lipids were varied in a systematic way and the resulting binary mixtures optionally were further supplied with 20 mol % cholesterol. The individual lipid mixtures were transformed into liposomes and used for the encapsulation of an active and control siRNA. When tested on HeLa cells, efficient and specific inhibition of the cell viability was observed for most of the tested formulations, as demonstrated in Example 5. The activity was not or only marginally affected by the presence of human or mouse serum, In Example 6, the anionic lipid CHEMS was combined with derivatives of PONA, wherein the guanido moiety was substituted by an amino group (PONamine) or an quarternized ammonium croup (PONammonium) as shown in the structures (21) and (23).

binations were only effective in some cases. The PONammonium:CHEMS combinations were not effective when an excess of the anionic lipid was used.

Moreover, out of the mixtures comprising an excess of the anionic lipid CHEMS, the transfection activity of the PONA:CHEMS combinations was only marginally affected by the presence of human or mouse serum, while the activity of PONamine:CHEMS combinations in was completed suppressed in the presence of mouse serum. The PONammonium formulations remained inactive in the presence of sera.

Combinations of PONA, PONamine or PONammonium with the phosphate lipids DOPA were also tested as further described in example 15. Both PONA and PONamine, but not PONammonium resulted in serum-resistant transfection of HeLa cells.

The combined data support a preferred uptake of lipid combinations comprising guanido lipids in combination with negatively charged, e.g. carboxyl or phosphate lipids. This may relate to the mechanistic considerations made further below. The constant and high activity of the formulations having an excess of the cationic lipid component may be due to electrostatic interaction between these particles and the cell surface, which however is unspecific. In line with this view is the fact that the activity of the cationic formulations did not depend on either the nature of the anionic or the cationic lipid.

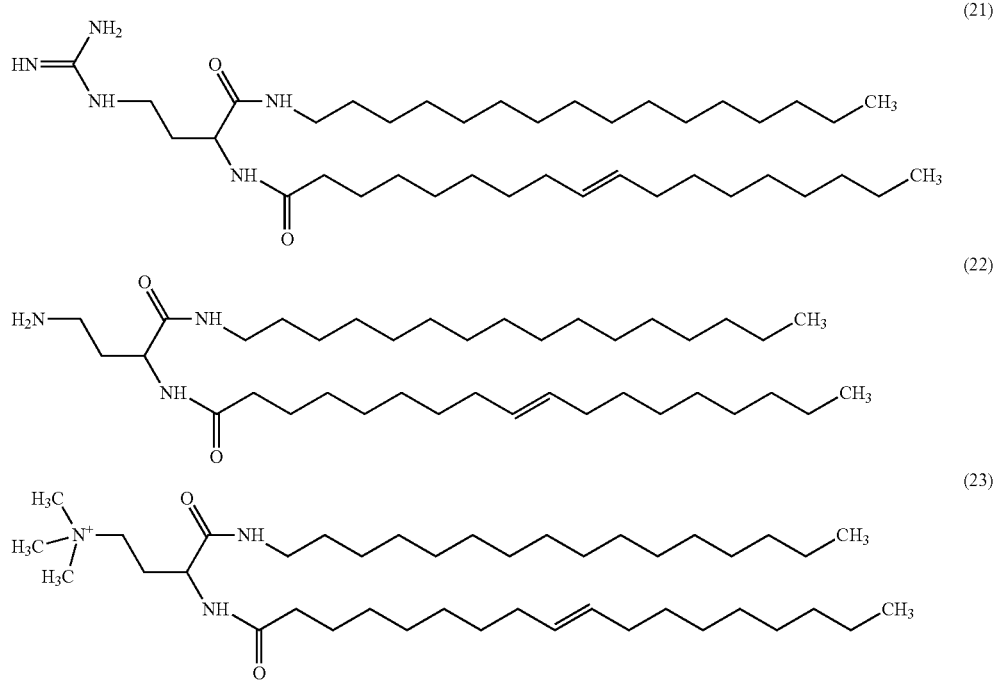

Again, the ratios between the anionic and cationic lipid components were systematically varied and 20% cholesterol was present in all lipid mixtures. The material was formulated into liposomes and used for the encapsulation of active and control siRNA. When tested on HeLa cells, efficient and specific inhibition of the cell viability was observed for all formulations comprising a molar excess of the cationic lipids. For mixtures comprising higher molar amounts of the anionic lipid CHEMS, the best activity was observed in combinations with PONA, while PONamine: CHEMS com- In further experiments, the guanido lipid PONA was combined with CHEMS, DMGS or DOGS. Again, a systematic variation of the ratios of both the anionic and cationic lipid compound in the respective binary mixtures was performed and the formulations were further supplied with 0, 20 or 40 mol % of cholesterol. When tested as above, the great majority of the formulations were active in inhibiting the cell proliferation of HeLa cells with an $IC_{50}$ being lower than 6 nM (see Example 7). A comparison between the concentrations needed for the efficacy of the active and inactive siRNA, however, revealed substantial differences between the formulations. A measure for such comparison is the ratio between the $IC_{50}$ values for both siRNA's, here expressed as SCR/PLK ratio. Only selected formulations reach values significantly higher than 5. Even more preferred formulations have SCR/PLK>10. All of these preferred formulations can be characterized by their ratio between the cationic and anionic lipid component, which is lower than 1.

This invention identifies specific lipid head group chemistry as critical for the uptake into certain cells in the presence of otherwise inhibitory sera. With preference, amphoteric combinations of anionic lipids comprising carboxyl groups and cationic lipids comprising charged imino moieties result in the desired properties. In contrast, cationic formulations comprising the same lipids do not depend on a specific head group chemistry and are less tolerated by cells.

Lipoprotein Binding

The lipoproteins competing with the transfection of liposomes, comprise a variety of structures, according to their density. These are known as chylomicrons, VLDL, LDL, IDL or HDL particles. In the endogenous pathway, chylomicrons are synthesized in the epithelial lining of the small intestine and are assembled using ApoB-48, a shorter variant of the ApoB gene product. Further exchange of lipoproteins with HDL particles leads to transfer of ApoC-II and ApoE to the chylomicron particle, the first mediating the activation of lipoprotein lipase, an enzyme needed for the release of lipids from the particle. The hydrolyzed chylomicrons form so called remnants which are taken up mainly in the liver via recognition of their ApoE portion. The synthesis, maturation, use and recycling of VLDL particles follows the very same pathway, but starts in the liver and is using the ApoB-100 protein as its structure forming unit. Again, ApoE mediates the eventual uptake and recycling of the VLDL-remnants, the so-called IDL particles. (see also http://en.wikipedia.org/wiki/Lipoprotein)

ApoE shares structural homology to the apolipoproteins A and C in that they all comprise amphipathic tandem repeats of 11 amino acids. Crystallographic data confirm the existence of extended amphipathic helical structures for ApoA-I and and ApoE fragment and also reveal a mixed charge organization on the polar face of these helices. These data are publicly available from the RCSB Protein Data Bank (available at www.rcsb.org/pdb/home/home.do) and entry 1AV1.pdb gives the protein structure of ApoA-l. The amino acids 129 to 166 of 1lpe.pdb represent the LDL-receptor binding fragment of ApoE. In contrast to their overall similarity, the three apolipoproteins display specific deviations when their amino acid composition is analyzed. In ApoE, arginine is the prevailing cationic amino acid in the tandem repeats. In contrast, ApoA has equal amounts of lysine and arginine, while ApoC has an excess of lysine residues.

TABLE 3

Analysis of the amino acid composition in tandem repeats of related apolipoproteins. Sequence data were obtained from Swiss-Protavailable at www.expasy.ch/sprot/sprot-top.html).

| Sequence | ApoAI | ApoE | ApoC-II |
|---|---|---|---|
| SwissProt Entry | P02647 | P02649 | P0265 |
| Endpoints | 68-267 | 80-255 | 23-101 |
| length | 199 | 175 | 78 |
| IP | 5.55 | 9.16 | 4.66 |
| # of lysine | 18 | 8 | 6 |
| # of arginine | 14 | 25 | 1 |
| # of histidine | 5 | 1 | 0 |
| # of aspartic acid | 10 | 8 | 4 |
| # of glutamic acid | 28 | 22 | 7 |
| Lysine (%) | 9% | 5% | 8% |
| Arginine (%) | 7% | 14% | 1% |
| Histidine (%) | 3% | 1% | 0% |
| Aspartic acid (%) | 5% | 5% | 5% |
| Glutamic acid (%) | 14% | 13% | 9% |

In summary, the polar surface of natural lipoproteins is covered with apolipoproteins, of which ApoE is a common binding motif for the cellular uptake of these particles. The water-exposed portions of ApoE represent a mosaic of anionic and cationic charges, wherein the anionic charges are created from the free carboxyl termini of aspartic and glutamic acid residues. The cationic charges comprise a mixture of amino and guanido groups with a very few imidazols being present.

In order to emulate the recognition pattern of the ApoE binding cassette on the surface of liposomes, different alternatives can be followed. It is possible to synthesize ApoE peptide fragment and graft such peptides on the surface of liposomes. This has been demonstrated by Mims et al., J Biol. Chem. 269, 20539 (1994); Rensen et al., Mol Pharmacol. 52, 445 (1997); Rensen et al., J. Lipid Res. 38, 1070 (1997); Sauer et al., Biochemistry 44, 2021 (2005) or Versluis et al., J Pharmacol. Exp. Ther 289, 1 (1999). However, the high cost associated with peptide synthesis and derivatization call for alternative approaches.

A direct presentation of the required charged moieties using mixtures of different charged lipids, potentially further comprising neutral lipids would yield a much simpler structure and eliminate the needs for costly peptide production and derivatizatior. A considerable challenge of such an approach is the planar diffusion of the charged groups within the lipid bilayee it was heretofore unclear whether the affinity of such a less organized assembly would effectively compete with the affinities provided by the authentic lipoproteins. Moreover, the oppositely charged lipid headgroups may form salt bridges with each other, while only few hydrogen bonds between functional groups are detected in the binding cassette of lipoproteins, e.g. ApoE. This may explain the activity of imino:phosphate lipid combinations such as GUADACADOPA or MPDACA:DOPA. While DOPA provides two negative charges under physiological conditions, steric hindrance disables the formation of a salt from one DOPA and two GUADACA lipids. As such, in these membranes the negatively charged salt between DOPA and GUADACA must co-exist with free GUADACA molecules, thereby facilitating the simultaneous presence of separated anionic and cationic elements in a common lipid assembly.

The theory above is mentioned without limiting the findings of this invention. Without wishing to be bound to this particular theory, one can assume that the combinations of charged imino lipids with negatively charged carboxyl or phosphate lipids emulate the surface properties of lipoproteins covered with ApoE. The particles can of course be used, developed and optimized without such knowledge.

The theoretical background may however be helpful to understand guiding principles or applicability of the vectors described in the various embodiments of this invention.

It is for example known, that lipoprotein receptors have different expression profiles in various cell types and such knowledge can be used to assess target cell populations for the liposomes of this invention.

The LDL-receptor is highly expressed on tumors and on the bronchoepithelial cells of the lung (see Su Al, Wiltshire T, Batalov S. et al (2004). Proc. Natl. Acad. SDI, U.S.A. 101 (16): 6062-7, also published at http://en.wikipedia.org/wikifFile:PBB_GE_LDLR_202068_s_at_tn.png)

The liposomes of this invention are thus specifically suited for applications in the field of oncology, but also for transfection of specific lung cells. While tumors are accessible from systemic circulation through the EPR-effect (enhanced permeability and retention), that is via leaky tumor vasculature, the bronchoepithelial cells can be targeted also from the airways.

In a specific embodiment of this invention, aerosols from liposomes comprising charged imino and carboxyl or phosphate lipids are thus used for inhaled dosage forms for the targeting of lung cells, in particular bronchoepithelial cells.

FIGURE LEGENDS

FIGS. 1-6 display the results of the screening experiment described in example 14. The nature of the cationic lipids is indicated in the smaller figures and other legends and axis are similar for all display items and are given in the separate smaller figure below. The double bars denote liposomes with 20% cholesterol (left bar) and 40% cholesterol (right bar), respectively.

Bars represent the IC50 values for the respective liposome/siRNA combinations under the experimental conditions for each figure, that is, either in the presence of absence of mouse serum. These IC50 values denote the concentrations needed for a half-maximal inhibition of the cell growth and are given in nM. The maximum concentrations of the test items were 40 and 36 nM for the absence or presence of mouse serum, respectively.

The order of the test items is as follows:

FIG. 1 the anionic lipid is CHEMS–no addition of mouse serum

FIG. 2 the anionic lipid is CHEMS+addition of mouse serum

FIG. 3 the anionic lipid is DMGS–no addition of mouse serum

FIG. 4 the anionic lipid is DMGS+addition of mouse serum

FIG. 5 the anionic lipid is DOGS–no addition of mouse serum

FIG. 6 the anionic lipid is DOGS+addition of mouse serum

EXAMPLES

The teachings of this invention may be better understood with the consideration of the following examples. However, these examples should by no means limit the teachings of this invention.

Example 1—Liposome Production, Characterization and Encapsulation of siRNA

Liposomes were prepared using methods as disclosed in WO071107304. More specifically, lipids were dissolved in isopropanol and liposomes were produced by adding siRNA solution in NaAc 20 mM, Sucrose 300 mM, pH 4.0 (pH adjusted with HAc) to the alcoholic lipid mix, resulting in a final alcohol concentration of 30%. The formed liposomal suspensions were shifted to pH 7.5 with twice the volume of $Na_2HPO_4$ 136 mM, NaCl 100 mM (pH 9), resulting in a final lipid concentration of 3 mM and a final isopropanol concentration of 10%.

Liposomes were characterized with respect to their particle size using dynamic light scattering (MALVERN 3000HSA).

Active siRNA: 21mer blunt ended targeting mouse and human ILK-1 mRNA as in Haupenthal et al., int. J. Cancer (2007), 121:206-210.

Control siRNA (SCR): 21 mer from the same source.

Example 2 General Cell Culture and Proliferation Assay

HeLa cells were obtained from DSMZ (German Collection of Micro Organism and Cell Cultures) and maintained in DMFM (Gibco-Invitrogen) and supplemented with 10% FCS. The cells were plated at a density of $2.5\times10^4$ cells/ml and cultivated in 100 μl medium at 37° C. under 5% $CO_2$. After 16 h, the liposomes containing siRNA were diluted and 10 μl were added to the cells to yield final concentrations between 0.4 to 100 nM Plk1 or scrambled siRNA; 10 μl dilution buffer were also added to untreated cells and into wells without cells. Cell culture dishes were incubated for 72 h at 37° C. under 5% $CO_2$ Cell proliferation/viability was determined by using the CellTiter-Blue Cell Viability assay (Promega, US) according to the instructions of the supplier.

Example 3—Inhibition of Transfection by Sera

Liposomes from DODAP:DMGS:Cholesterol (24:36:40 mol %) were loaded with active and control siRNA as above and 25 μl of the liposomes were incubated with 75 μl sera from different species (SIGMA-Aldrich) for 30 min. Following that, liposomes were added to the cells, incubation was continued for 72 h and cell viability was determined as above.

When incubated without serum, administration of the active siRNA results in a strong inhibition of cell proliferation. As demonstrated in the Table 7 below, this process is inhibited in by the addition of sera.

TABLE 7

Inhibition of cellular transfection by sera of different origin.

| siRNA type | siRNA concentration | Serum | Cell viability (%) |
|---|---|---|---|
| PLK1 | 50 nM | no | 7 |
| PLK1 | 50 nM | Human | 98 |
| PLK1 | 50 nM | Hamster | 80 |
| PLK1 | 50 nM | Rat | 108 |
| PLK1 | 50 nM | Mouse | 102 |
| No | No | No | 100 |

Example 4—Inhibition is Lipoprotein Dependent

Liposomes as in Example 3 were incubated with human serum devoid of certain complement factors or lipoproteins (SIGMA-Aldrich) as above and analyzed for their ability to mediate the RNAi effect on HeLa cells.

As demonstrated in Table 8, the efficacy of transfection can be restored by a depletion of lipoproteins. Removal of complement factors was ineffective.

TABLE 8

Restoration of cellular transfection in sera being deficient of various factors.

| siRNA type | siRNA concentration | Serum | Cell viability (%) |
|---|---|---|---|
| PLK1 | 50 nM | no | 7 |
| PLK1 | 50 nM | Human, complete | 98 |
| PLK1 | 50 nM | Human, no C3 complement factor | 91 |
| PLK1 | 50 nM | Human, no C9 complement factor | 98 |
| PLK1 | 50 nM | Human, lipoprotein deficient | 18 |
| No | No | No | 100 |

Example 5—Serum Resistant Transfection Using a Guanido Lipid

A series of liposomes was constructed from PONA:Anionic Lipid:Cholesterol (x:y:20 mol %) and loaded with active and control siRNA as in Example 1. Within that series, the ratio between the cationic component PONA and the anionic lipids CHEMS or DMGS was systematically varied between 0.33 and 2 as indicated in the table. Liposomes having a ratio of the cationic anionic lipid of 1 or greater were further supplied with 2 mol % DMPE-PEG2000 (Nippon Oils and Fats) to avoid aggregation of the particles. This modification is indicated by a "+" in the table. Control reactions with particles having C/A<1 did not reveal a change of transfection properties in the presence or absence of PEG lipids.

HeLa cells were grown and maintained as in Example 2 and sera of human or mice origin (SIGMA-Aldrich) was added directly to the cells for 120 min. Following that, the liposomes were added to the cells in concentrations between 50 µM and 50 nM, incubation was continued for 72 h and cell viability was determined as above. The efficacy of transfection is expressed here as $IC_{50}$, the concentration needed to inhibited cell proliferation by 50%, Low IC50 values therefore represent highly effective transfection.

It becomes apparent from the results in the Table 9, that the addition of sera only marginally affects the transfection of siRNA mediated by the liposomes of the example. Some inhibition is still observed for liposomes from PONA:CHEMS comprising low amounts of the anionic lipid (ratios 0.33 and 0.5, particular strong inhibition with mouse serum).

TABLE 9

Efficacy of transfection of liposomes comprising guanido moieties in the presence of sera.

| | Ratio cationic/anionic lipid | | | | | | | |
|---|---|---|---|---|---|---|---|---|
| | 0.33 | 0.50 | 0.67 | 0.82 | 1+ | 1.22+ | 1.5+ | 2+ |
| | CHEMS | | | | | | | |
| No Serum | 38.54 | 1.21 | 0.40 | 0.56 | 1.83 | 1.61 | 0.70 | 1.42 |
| Human Serum | 199.00 | 2.10 | 0.62 | 1.13 | 2.16 | 1.92 | 1.70 | 1.83 |
| Mouse Serum | 199.00 | 50.00 | 1.56 | 1.94 | 2.47 | 1.90 | 0.76 | 1.44 |
| | DMGS | | | | | | | |
| No Serum | | 0.23 | 0.54 | 0.01 | 0.01 | | | |
| Human Serum | | 1.50 | 2.39 | 2.88 | 2.21 | | | |
| Mouse Serum | | 0.67 | 0.69 | 1.41 | 1.81 | | | |

Example 6—Criticality of the Guanido Head Group

Series of liposomes having systematically varied ratios between the cationic and anionic lipid components were produced and loaded with siRNA as in Example 5. The cationic lipid components were PONA, PONamine and PONammonium, the anionic lipid was CHEMS and the cholesterol content was fixed to 20 mol %. Liposomes having a ratio of the cationic anionic lipid of 1 or greater were further supplied with 2 mol % DMPE-PEG2000 (Nippon Oils and Fats) to avoid aggregation of the particles. This modification is indicated by a "+" in the table.

HeLa cells were grown and maintained as in Example 2 and sera of human or mice origin (SIGMA-Aldrich) was added directly to the cells for 120 min. Following that, the liposomes were added to the cells in concentrations between 50 pM and 50 nM, incubation was continued for 72 h and cell viability was determined as above. The efficacy of transfection is expressed here as $IC_{50}$ as in Example 5.

It becomes apparent from the data in Table 10, that only PONA, but neither PONamine and even less so PONammonium mediates the transfection of HeLa cells in the presence of serum. This is most striking in the case of mouse serum, which inhibits the transfection more aggressively. An excess of the cationic lipid components to some extent compensate the serum mediated loss of activity, but may be due to unspecific electrostatic adsorption of these liposomes to the cells.

TABLE 10

Criticality of the guanido head group for the serum restant transfection of cells.

| | C/A ratio | | | | | | | |
|---|---|---|---|---|---|---|---|---|
| | 0.33 | 0.5 | 0.67 | 0.82 | 1+ | 1.22+ | 1.5+ | 2+ |
| | PONA | | | | | | | |
| no serum | 42.9 | 1.8 | 0.6 | 1.0 | 4.1 | 5.4 | 2.4 | 6.8 |
| human serum | 80.0 | 2.5 | 2.2 | 2.0 | 1.8 | 2.8 | 6.2 | 5.2 |
| mouse serum | 80.0 | 31.1 | 55.0 | 5.7 | 2.1 | 5.3 | 8.1 | 7.5 |
| | PONamine | | | | | | | |
| no serum | 3.1 | 65.0 | 7.5 | 100.0 | 3.0 | 5.2 | 3.0 | 2.5 |
| human serum | 100.0 | 55.0 | 11.9 | 100.0 | 2.2 | 2.8 | 6.1 | 5.1 |
| mouse serum | 70.0 | 100.0 | 100.0 | 100.0 | 75.0 | 70.0 | 39.3 | 8.7 |

TABLE 10-continued

Criticality of the guanido head group for the serum restant transfection of cells.

| | C/A ratio | | | | | | | |
|---|---|---|---|---|---|---|---|---|
| | 0.33 | 0.5 | 0.67 | 0.82 | 1+ | 1.22+ | 1.5+ | 2+ |
| | PONammonium | | | | | | | |
| no serum | 80.0 | 100.0 | 90.0 | 90.0 | 65.0 | 9.5 | 9.5 | 5.2 |
| human serum | 95.0 | 90.0 | 90.0 | 80.0 | 90.0 | 11.8 | 12.4 | 15.7 |
| mouse serum | 85.0 | 100.0 | 100.0 | 100.0 | 100.0 | 90.0 | 75.0 | 55.0 |

Example 7—Optimization of the Liposome Composition

Series of liposomes having systematically varied ratios between the cationic and anionic lipid components were produced and loaded with siRNA as in Example 5. The cationic lipid component was PUNA, the anionic lipids were CHEMS, DMGS or DOGS and the cholesterol content was varied between 0 and 40 mol %. Liposomes having a ratio of the cationic anionic lipid of 1 or greater but also some of the other liposomes were further supplied with 2 mol % DMPE-PEG2000 (Nippon Oils and Fats) to avoid aggregation of the particles. This modification is indicated by a "+" in the table.

HeLa cells were grown and maintained as in Example 2 and liposomes were added to the cells in concentrations between 6 nM and 200 nM, incubation was continued for 72 h and cell viability was determined as above. The efficacy of transfection is expressed here as $IC_{50}$ as in the examples above. In addition, the $IC_{50}$ was determined for the liposomes carrying the inactive siRNA (SCR) and the ratio between $IC_{50}$ (SCR) and $IC_{50}$ (PLK1) was determined. A high value for this parameter indicates a very specific inhibition of the cellular viability by the PLK1 siRNA, low unspecific effects contributed by the carrier and low levels of cytotoxicity in general.

TABLE 11

Optimization results for CHEMS. Lowest and highest detectable $IC_{50}$ values are 6 and 200 nM, respectively.

| | C/A | 0.33 | 0.33+ | 0.5 | 0.5+ | 0.67 | 0.67+ | 0.82 | 0.82+ | 1+ | 1.22+ | 1.5+ | 2+ |
|---|---|---|---|---|---|---|---|---|---|---|---|---|---|
| PLK | 0% Chol | 44 | 77 | 6 | 6 | 6 | 6 | 6 | 6 | 6 | 6 | 6 | 6 |
| | 20% Chol | 54 | 79 | 6 | 6 | 6 | 6 | 6 | 6 | 6 | 6 | 6 | 6 |
| | 40% Chol | 67 | 94 | 6 | 6 | 6 | 6 | 6 | 6 | 6 | 6 | 6 | 6 |
| SCR | 0% Chol | 90 | 86 | 113 | 152 | 23 | 200 | 16 | 21 | 15 | 16 | 14 | 11 |
| | 20% Chol | 73 | 90 | 109 | 128 | 200 | 200 | 26 | 23 | 21 | 11 | 16 | 10 |
| | 40% Chol | 94 | 117 | 198 | 200 | 200 | 200 | 6 | 6 | 30 | 14 | 27 | 12 |
| SCR/ | 0% Chol | 2.05 | 1.12 | 18.86 | 25.33 | 3.81 | 83.33 | 2.60 | 3.52 | 2.50 | 2.68 | 2.30 | 1.84 |
| PLK | 20% Chol | 1.37 | 1.14 | 18.10 | 21.39 | 83.33 | 83.33 | 4.26 | 3.77 | 3.45 | 1.84 | 2.65 | 1.69 |
| | 40% Chol | 1.40 | 1.24 | 32.96 | 83.33 | 83.33 | 83.33 | 1.00 | 1.00 | 5.00 | 2.39 | 4.48 | 1.97 |

TABLE 12

Optimization results for DMGS. Lowest and highest detectable $IC_{50}$ values are 6 and 200 nM, respectively.

| | C/A | 0.33 | 0.5 | 0.67 | 0.8.2 | 1+ | 1.22 | 1.5+ | 2+ |
|---|---|---|---|---|---|---|---|---|---|
| PLK | 0% Chol | 98 | 200 | 200 | 188 | 6 | 6 | 6 | 6 |
| | 20% Chol | 6 | 6 | 6 | 6 | 6 | 6 | 6 | 6 |
| | 40% Chol | 6 | 6 | 6 | 6 | 6 | 6 | 6 | 6 |
| SCR | 0% Chol | 200 | 200 | 200 | 158 | 14 | 6 | 10 | 14 |
| | 20% Chol | 200 | 54 | 8 | 8 | 13 | 9 | 9 | 10 |
| | 40% Chol | 155 | 23 | 11 | 6 | 6 | 14 | 9 | 12 |
| SCR/PLK | 0% Chol | 5.11 | no effect | no effect | 0.84 | 2.26 | 1.00 | 1.66 | 2.36 |
| | 20% Chol | 83.33 | 9.01 | 1.27 | 1.26 | 2.20 | 1.55 | 1.45 | 1.69 |
| | 40% Chol | 25.85 | 3.90 | 1.83 | 1.00 | 1.00 | 2.27 | 1.54 | 1.97 |

TABLE 13

Optimization results for DOGS. Lowest and highest detectable IC$_{50}$ values are 6 nM, and 200 respectively.

|  | C/A | 0.33 | 0.5 | 1 | 0.67 | 0.82 | 1.22+ | 1.5+ | 2+ |
|---|---|---|---|---|---|---|---|---|---|
| PLK | 0% Chol | 200 | 200 | 200 | 200 | 6 | 6 | 6 | 6 |
|  | 20% Chol | 22 | 200 | 200 | 200 | 6 | 6 | 6 | 6 |
|  | 40% Chol | 6 | 170 | 200 | 200 | 6 | 6 | 6 | 6 |
| SCR | 0% Chol | 200 | 200 | 200 | 200 | 14 | 10 | 16 | 10 |
|  | 20% Chol | 200 | 200 | 200 | 200 | 21 | 10 | 12 | 8 |
|  | 40% Chol | 15 | 197 | 200 | 200 | 12 | 7 | 9 | 9 |
| SCR/PLK | 0% Chol | no effect | no effect | no effect | no effect | 2.40 | 1.59 | 2.65 | 1.63 |
|  | 20% Chol | 22.42 | no effect | no effect | no effect | 3.45 | 1.65 | 2.07 | 1.29 |
|  | 40% Chol | 2.48 | 1.16 | no effect | no effect | 1.93 | 1.09 | 1.48 | 1.55 |

Example 6—Liposomes Comprising a Pyridinium Lipid

SAINT-18 was used as the cationic lipid, its methylated pyridinium structure provides a charged imino moiety. CHEM, DMGS and DOGS were individually used as anionic lipids providing the carboxyl functional group. Series of liposomes having systematically varied ratios between the cationic and anionic lipid components were produced and loaded with siRNA as in Example 5. The lipid mixture was further supplied with 20 or 40 mol % cholesterol. Liposomes having a ratio of the cationic:anionic lipid of 1 or greater were further supplied with 2 mol % DMPE-PEG2000 (Nippon Oils and Fats) to avoid aggregation of the particles. This modification is indicated by a in the table.

HeLa cells were grown and maintained as in Example 2 and liposomes were added to the cells in concentrations between 50 pM and 50 nM, incubation was continued for 72 h and cell viability was determined as above. The efficacy of transfection is expressed here as IC$_{50}$ as in the examples above. In addition, the IC$_{50}$ was determined for the liposomes carrying the inactive siRNA (SCR) and the ratio between IC$_{50}$ (SCR) and IC$_{50}$ (PLK1) was determined. A high value for this parameter indicates a very specific inhibition of the cellular viability by the PLK1 siRNA, low unspecific effects contributed by the carrier and low levels of cytotoxicity in general.

TABLE 14 transfection results for liposomes from SAINT-18, CHEMS and cholesterol

|  | C/A ratio | 0.33 | 0.5 | 0.67 | 0.82 | 1+ | 1.22+ | 1.5+ | 2+ |
|---|---|---|---|---|---|---|---|---|---|
| lipid anion CHEMS no serum | | | | | | | | | |
| PLK1 | 20% Chol | 2.2 | no eff. | 1.7 | 33.9 | 17.8 | 7.2 | 4.1 | 2.7 |
|  | 40% Chol | 7.8 | no eff. | 1.5 | 32.0 | 7.2 | 4.4 | 2.1 | 6.4 |
| SCR | 20% Chol | no eff. | no eff. | 11.9 | no eff. | 37.4 | 19.6 | 20.7 | 29.0 |
|  | 40% Chol | no eff. | no eff. | no eff. | no eff. | no eff. | 16.9 | 18.6 | 28.0 |
| SCR/ | 20% Chol | >22.7 |  | 7.2 | >1.5 | 2.1 | 2.7 | 5.0 | 10.6 |
| PLK-1 | 40% Chol | >26.4 |  | 32.5 | >1.6 | >7.0 | 3.9 | 8.7 | 4.4 |
| lipid anion CHEMS plus mouse serum | | | | | | | | | |
| PLK1 | 20% Chol | no eff. | no eff. | 14.4 | no eff. | no eff. | no eff. | no eff. | 31.7 |
|  | 40% Chol | no eff. | no eff. | no eff. | no eff. | no eff. | no eff. | 35.5 | 23.1 |
| SCR | 20% Chol | no eff. | no eff. | no eff. | no eff. | no eff. | no eff. | no eff. | no eff. |
|  | 40% Chol | no eff. | no eff. | no eff. | no eff. | no eff. | no eff. | 41.5 | 38.1 |
| SCR/ | 20% Chol |  |  | >3.5 |  |  |  |  | >1.6 |
| PLK-1 | 40% Chol |  |  |  |  |  |  | 1.2 | 1.6 |

TABLE 15 transfection results for liposomes from SAINT-18. DMGS and cholesterol

|  | C/A ratio | 0.33 | 0.5 | 0.67 | 0.82 | 1+ | 1.22+ | 1.5+ | 2+ |
|---|---|---|---|---|---|---|---|---|---|
| lipid anion DMGS, no serum | | | | | | | | | |
| PLK1 | 20% Chol | 0.8 | 2.3 | 1.7 | 43.6 | 24.3 | 7.5 | 5.2 | 3.8 |
|  | 40% Chol | 1.6 | 2.3 | 1.8 | 2.2 | 11.4 | 8.9 | 3.8 | 5.8 |
| SCR | 20% Chol | 7.7 | 8.2 | 5.3 | 36.0 | 28.1 | 27.6 | 10.5 | 10.3 |
|  | 40% Chol | 4.7 | no eff. | 22.6 | 5.7 | 27.7 | 28.5 | 8.1 | 8.2 |
| SCR/ | 20% Chol | 9.2 | 3.6 | 3.1 | 0.8 | 1.2. | 3.7 | 2.0 | 2.7 |
| PLK-1 | 40% Chol | 2.9 | >22.1 | 12.6 | 2.5 | 2.4 | 3.2 | 2.1 | 1.4 |
| lipid anion DMGS; plus mouse serum | | | | | | | | | |
| PLK1 | 20% Chol | 4.0 | 8.0 | 2.7 | no eff. | 26.5 | 28.8 | no eff. | no eff. |
|  | 40% Chol | 2.0 | 2.2 | 1.6 | 1.6 | no eff. | 21.0 | no eff. | no eff. |

TABLE 15-continued transfection results for liposomes from SAINT-18. DMGS and cholesterol

| | C/A ratio | 0.33 | 0.5 | 0.67 | 0.82 | 1+ | 1.22+ | 1.5+ | 2+ |
|---|---|---|---|---|---|---|---|---|---|
| SCR | 20% Chol | 10.1 | no eff. | 23.4 | no eff. | 29.1 | 31.2 | 25.7 | 28.4 |
| | 40% Chol | 7.7 | 18.0 | 25.8 | 6.3 | 28.0 | 37.4 | 31.7 | 25.7 |
| SCR/ | 20% Chol | 2.5 | >6.2 | 8.6 | | 1.1 | 1.1 | | |
| PLK-1 | 40% Chol | 3.9 | 8.0 | 16.5 | 3.9 | | 1.8 | | |

TABLE 16 transfection results for liposomes from SAINT-18, DOGS and cholesterol

| | C/A ratio | 0.33 | 0.5 | 0.67 | 0.82 | 1+ | 1.22+ | 1.5+ | 2+ |
|---|---|---|---|---|---|---|---|---|---|
| | | lipid anion DOGS, no serum | | | | | | | |
| PLK1 | 20% Chol | 36.9 | 38.0 | no eff. | no eff. | 9.2 | 8.1 | 7.0 | 6. |
| | 40% Chol | 6.9 | 19.4 | no eff. | no eff. | 22.7 | 8.7 | 6.6 | 8.5 |
| SCR | 20% Chol | no eff. | no eff. | no eff. | no eff. | 27.5 | 20.5 | 10.2 | 25.9 |
| | 40% Chol | no eff. | no eff. | no eff. | no eff. | no eff. | no eff. | no eff. | no eff. |
| SCR/ | 20% Chol | >1.4 | >1.3 | | | 3.0 | 2.5 | 1.5 | 4.3 |
| PLK-1 | 40% Chol | >7.3 | >2.6 | | | >2.2 | >5.7 | >7.6 | >5.9 |
| | | lipid anion DOGS, plus serum | | | | | | | |
| PLK-1 | 20% Chol | 2.2 | 18.4 | no eff. | no eff. | 27.5 | 30.5 | 26.3 | 28.1 |
| | 40% Chol | 2.7 | 7.7 | no eff. | no eff. | 27.4 | 29.2 | 30.4 | 30.8 |
| SCR | 20% Chol | no eff. | 2.8 | no eff. | no eff. | 32.6 | 34.4 | 30.9 | 33.2 |
| | 40% Chol | no eff. | 8.2 | no eff. | no eff. | 30.6 | no eff. | no eff. | 42.8 |
| SCR/ | 20% Chol | 1.3 | >2.7 | | | 1.2 | 1.1 | 1.2 | 1.2 |
| PLK-1 | 40% Chol | >18.6 | 1.1 | | | 1.1 | >1.7 | >1.6 | 1.4 |

As it becomes clear from the data in tables 14 to 16, a large number of amphoteric liposomes facilitate the transfection of cells even in the presence of mouse serum. Particularly useful are liposomes comprising SAINT-18 in combination with the diacylglycerols DMGS and DOGS, while the combination with CHEMS was only effective at C/A=0.67. As with the PONA combinations, the amphoteric constructs transfect the cells with high specificity, while the compositions having >1 do not provide a highly specific transfection as indicated by SCR/PLK1 being below 2.

Other embodiments and uses of the invention will be apparent to those skilled in the art from consideration of the specification and practice of the invention disclosed herein. The specification and examples should be considered exemplary only with the true scope and spirit of the invention indicated by the following claims.

Example 9—Zeta Potential Measurements 9.1 Analysis of the Zeta Potential for Liposomes Formed from PONA:CHEMS:CHOL 100 µl of a lipidmix comprising x Mol % PONA, y mol % CHEMS and 20 Mol % cholesterol (20 mM total lipid concentration, solvent: isopropanol) was injected in 900 µl of a buffer comprising 10 mM acetic acid and 10 mM phosphoric acid pH4, X and Y, the molar percentages for PONA and CHEMS were adjusted to yield the C/A ratios in table 17. The suspension was immediately vortexed and 3 mL of a pH adjusting buffer was added. Buffers were selected from the group of 50 mM acetic acid and 50 mM phosphoric acid, adjusted to pH 4, 5, 6.5 or 7.5 using NaOH or 50 mM $Na_2HPO_4$/50 mM sodium acetate pH9.4. The mixing pH is was recorded and is given in the table 17 below together with the zeta potentials of the resulting lipid particles that were monitored using a Zetasizer HSA3000.

TABLE 17

Zeta Potentials for lipid particles from PONA:CHEMS:CHOL

| | C/A ratio | | | | | | |
|---|---|---|---|---|---|---|---|
| Final pH | 0.5 | 0.67 | 0.82 | 1.00 | 1.22 | 1.5 | 2.00 |
| 7.56 | −54.40 | −58.90 | −58.20 | −61.80 | −21.80 | 22.60 | #NV |
| 7.20 | −48.47 | −46.00 | −44.90 | −50.00 | −21.10 | 14.97 | #NV |
| 6.32 | −44.33 | −37.07 | −31.37 | 0.64 | 23.43 | 9.60 | #NV |
| 4.84 | 19.67 | 18.00 | 22.15 | 31.80 | 32.77 | 32.57 | 28.37 |
| 3.93 | 35.53 | 41.73 | 43.75 | 46.63 | 46.20 | 43.40 | 43.23 |

Clearly, the particles display amphoteric character even for mixtures having a C/A of 1.22, that is, greater than 1. Particles having a C/A of 0.67, 0.82 or 1 were also produced at pH7.4 and subsequently exposed to lower pH. There were no apparent changes to the zeta potentials shown in table 17.

9.2 Zeta Potential Measurements for Combinations Wherein DOPA is the Anionic Lipid Lipid particles were also prepared from binary mixtures of GUADACA and DOPA, an imino/phosphate combination of lipid head groups. The particles were prepared in the same fashion as described in 9.1 and the zeta potentials of table 18 were recorded for mixtures having different C/A ratios:

TABLE 18

Zeta Potentials for lipid particles from GUADACA:DOPA

| C/A final pH | 0.65 | 0.75 | 0.98 | 1.16 | 1.4 |
|---|---|---|---|---|---|
| 4.5 | 21 | 13 | 38 | 46 | 51 |
| 5.32 | −24 | 22 | 20 | 33 | 35 |

TABLE 18-continued

| Zeta Potentials for lipid particles from GUADACA:DOPA | | | | | |
|---|---|---|---|---|---|
| 6.25 | −8 | −45 | −30 | 2 | 24 |
| 7.02 | −61 | −67 | −8 | −56 | −6 |
| 7.81 | −67 | −78 | −76 | −65 | −21 |

As with the particles obtained in 9.1, particles with amphoteric character are also obtained with C/A>1. Still, the drift in the isoelectric point follows the expectations.

9.3 Zeta Potential Measurements for DOTAP:CHEMS:CHOL

For comparison, the same measurements were performed with lipid mixtures wherein PONA was substituted by DOTAP. The results are shown in table 19. In contrast to PONA: CHEMS, amphoteric particles from DOTAP: CHEMS are only found at C/A<1

TABLE 19

| Zeta potential for lipid particles from DOTAP:CHEMS:CHOL | | | | |
|---|---|---|---|---|
| Ratio C/A Final pH | 0.67 | 0.82 | 1 | 1.22 |
| 7.56 | −37.7 | −21.63 | 4.9 | 13.25 |
| 7.20 | −50.17 | −24.1 | #NV | 12.55 |
| 6.32 | #NV | #NV | 11.43 | 7.37 |
| 4.84 | 25.6 | 32.1 | 20.27 | 9.3 |
| 3.93 | 52.13 | 43.93 | 47.77 | 12.15 |

Example 10—Synthesis of CHOLGUA 25 g cholesterolchloroformiate and 50 equivalents (eq.) ethylendiamine were dissolved in dichloromethane and allowed to react for 6 h at 20° C. The aminoethylcarbamoylcholestererol was isolated using chromatography and crystallization. Yield was 28.7 g, purity 90%.

CHOLGUA was synthesized from the aminaethylcarboarnoyl-cholesterol isolated before. 30 g of the substance were incubated with 1.5 eq. of 1H-pyrazole-1-carboxamidinium hydrochloride and 4 eq. N,N-diisopropylethylamin in dichloromethane/ethenol for 16 h at 20° C., after which the product was isolated by chromatography. Purity was 95%, Yield 16.5 g.

Example 11—Synthesis of DACA, PDACA and MPDACA 42.4 g of oleyl alcohol, 2.5 eq. of diisoproylazodicarboxylate, 2.5 eq, triphenylphosphine and 5 eq. LiI were reacted in tetrahydrofuran (THF) for 24 h at 20° C. Oleyliodid was isolated by chromatography with a purity of 90%, yield was 13.4 g.

In a second step, 10 g oleic acid were mixed with 2.2 eq. of lithiumdiisopropylamide in THF for 0.5 h at 20° C., after which 1 eq. oleyliodide was added. The mixture was incubated for 2 h at 20° C. and DACA purified from the reaction mix using chromatography. Purity was 95%, Yield 14.96 g, For the synthesis of PDACA, 2 g of DACA, 1.2 eq. of 4-picolylamine, 1.4 eq, of O-benzotriazole-1-yl-N,N,N',N'-tetramethyluronium tetrafluoroborate and 4 eq. of N-mathylmorpholine were mixed in THF for 24 h at 20° C. The reaction mixture was purified including chromatography. Purity of PDACA was 95%, yield was 1.72 g.

For the synthesis of MPDACA, 2 g of PDACA was dissolved in THF together with 2 eq. of dimethylsulphate and the mixture was incubated for 16 h at 20° C., after which MPDACA was purified by chromatography. Purity of MPDACA: 95%, Yield:1.71 g

Example 12—Synthesis of GUADACA

In a first step, 3.5 g DACA and 1.5 eq. of 1,1'-carbonyldiimidazol were dissolved in dichloromethane and incubated for 16 h at 20° C., after which 30 eq. ethylenediamine were added. The reaction mixture was incubated for 4 h at 20° C. after which aminoethyl-DACA was purified including chromatography. Purity was 90%, Yield 3.2 g.

GUADACA was synthesized from aminoethyl-DACA and for that, 3.2 g of aminoethyl-DACA, 2.5 eq. 1H-pyrazole-1-carboxamidine hydrochloride and 12 eq. N,N-diisopropylethylamine were incubated for 3 h at 20° C., after which GUADACA was isolated. Purity: 95%, Yield: 2.24 g.

Example 13—Synthesis of BADACA

BADACA was synthesized from DACA according to the following procedure: 4.1:5 g DACA, 1.2 eq, p-aminobenzamidine, 1.2 eq. N,N'-dicyclohexylcarbodiimid and 3 eq. of 4-Dimethylaminopyridine were mixed in dry dimethylformamide and incubated for 16 h at 70° C. BADACA was isolated from the reaction using chromatography. Purity: 95%, Yield: 1.62 g

Example 14 Serum Resistant Transfection of DACA or Cholesterol Based Cationic Lipids in Combination with Carboxyl Lipids Series of liposomes having systematically varied ratios between the cationic and anionic lipid components were produced and loaded with siRNA as in Example 5. The cationic lipid components were CHOLGUA, CHIM, DC-CHOL, TC-CHOL, GUADACA, MPDACA, BADACA end PDAGA. The anionic lipids were CHEMS, DMGS or DOGS and the cholesterol content was either 20 or 40 mol %, all lipid mixtures are identified in the data tables. Liposomes having a ratio of the cationic: anionic lipid of 1 or greater (C/A>=1) were further supplied with 1.5 mol % DMPE-PEG2000 (Nippon Oils and Fats).

HeLa cells were grown and maintained as in Example 2 and mouse serum (SIGMA-Aldrich) was added directly to the cells for 120 min. Following that, the liposomes were added to the cells, incubation was continued for 72 h and cell viability was determined as above. The highest concentrations of liposomes were 40 nM and 36 nM for experiments in the absence or presence of mouse serum, respectively. The efficacy of transfection is expressed here as $IC_{50}$ (in nM siRNA) as in Example 5. All results from this screening experiment are shown in FIGS. 1-6.

Many of the transfecting mixtures resulted in very potent transfection of HeLa cells with siRNA, as indicated by the very low IC50 values. Combinations of lipids comprising imino lipids such as CHOLGUA, but more so MPDACA, GUADACA or PONA remain potent transfectants even in the presence of mouse serum.

Example 15—Serum Resistant Transfection of Several Cationic Lipids in Combination with Phosphate Lipid Series of liposomes having C/A ratios of either 0.75 or 1 were produced and loaded with siRNA as in Example 5. The cationic lipid components were CHOLGUA, CHIM, DC-CHOL, GUADACA, MPDACA, BADACA, PONA, DOTAP or DODAP. The anionic lipid was DOPA and the cholesterol content was 40 mol %, all lipid mixtures are identified in table 20. Liposomes were further supplied with 1.5 mol % DMPE-PEG2000 (Nippon Oils and Fats).

HeLa cells were grown and maintained as in Example 2 and mouse serum (SIGMA-Aldrich) was added directly to the cells for 120-min. Following that, the liposomes were added to the cells, incubation was continued for 72 h and cell viability was determined as above. The efficacy of transfection is expressed here as $IC_{50}$ (in nM of siRNA) as in Example 5.

Many of the transfecting mixtures resulted in very potent transfection of HeLa cells with siRNA, as indicated by the very low IC50 values. Combinations of lipids comprising imino lipids such as CHOLGUA, but more so MPDACA, GUADACA or PONA remain potent transfectants even in the presence of mouse serum.

TABLE 20

IC50 values (nM siRNA) for various liposomes in the presence and absence of mouse serum. Serum inhibition "not potent" refers to a lack of minimum potency in the presence of mouse serum. in these cases the inhibition factor cannot be defined. The highest concentration of siRNA in the test was 146 nM.

| | | −mouse serum | | +mouse serum | | |
| --- | --- | --- | --- | --- | --- | --- |
| C/A | Cation | IC50 PLK1 | IC50 Scr. | IC50 PLK1 | IC50 Scr. | serum inhibition |
| 0.75 | CholGUA | 8 | 160 | 104 | 146 | 12 |
| | CHIM | 26 | 160 | 146 | 146 | not potent |
| | DC-Chol | 28 | 160 | 146 | 146 | not potent |
| | MPDACA | 5 | 67 | 10 | 146 | 2 |
| | GUADACA | 6 | 39 | 26 | 146 | 4 |
| | BADACA | 159 | 160 | 146 | 146 | not potent |
| | PONA | 6 | 24 | 146 | 146 | not potent |
| | DOTAP | 21 | 152 | 146 | 146 | not potent |
| | DODAP | 160 | 160 | 146 | 146 | not potent |
| 1 | CholGUA | 9 | 141 | 125 | 146 | 14 |
| | CHIM | 33 | 160 | 146 | 146 | not potent |
| | DC-Chol | 29 | 160 | 146 | 146 | not potent |
| | MPDACA | 12. | 100 | 4 | 146 | 0.3 |

TABLE 20-continued

IC50 values (nM siRNA) for various liposomes in the presence and absence of mouse serum. Serum inhibition "not potent" refers to a lack of minimum potency in the presence of mouse serum. in these cases the inhibition factor cannot be defined. The highest concentration of siRNA in the test was 146 nM.

| | | −mouse serum | | +mouse serum | | |
| --- | --- | --- | --- | --- | --- | --- |
| C/A | Cation | IC50 PLK1 | IC50 Scr. | IC50 PLK1 | IC50 Scr. | serum inhibition |
| | GUADACA | 9 | 89 | 7 | 146 | 1 |
| | BADACA | 38 | 160 | 146 | 146 | not potent |
| | PONA | 2 | 66 | 21 | 146 | 10 |
| | DOTAP | 13 | 160 | 76 | 146 | 6 |
| | DODAP | 94 | 160 | 146 | 146 | not potent |

Example 16—Serum Resistant Transfection is Poor in the Absence of Negatively Charged A series of liposomes was produced from cationic lipids and cholesterol as a neutral lipid. No anionic lipids were used in these preparations. The cationic lipid components were CHOLGUA, CHIM, DC-CHOL, ADACA, GUADACA, MPDACA, BADACA, PONA, DOTAP and DODAP and the liposomes were produced with the procedure described in example 5.

The cholesterol content was 40 mol % and liposomes were further supplied with 1.5 mol % DMPE-PEG2000 (Nippon Oils and Fats) to avoid aggregate formation in the presence of siRNA.

HeLa cells were grown and maintained as in Example 2 and mouse serum (SIGMA-Aldrich) was added directly to the cells for 120 min. Following that, the liposomes were added to the cells, incubation was continued for 72 h and cell viability was determined as above. The efficacy of transfection is expressed here as $IC_{50}$ (in nM of siRNA) as in Example 5.

The results obtained are shown in table 21 below. In all cases, the transfection efficacy is substantially lower than that of the mixtures further comprising an anionic lipid. With the exception of GUADACA or PONA, there was no activity detectable in the presence of mouse serum.

TABLE 21

IC50 values (nM siRNA) for various liposomes in the presence and absence of mouse serum. Serum inhibition "not potent" refers to a lack of minimum potency in the presence of mouse serum, in these cases the inhibition factor cannot be defined. The highest concentration of siRNA in the test was 160 or 146 nM in the absence of presence of mouse serum, respectively.

| | no mouse serum | | with mouse serum | | serum |
| --- | --- | --- | --- | --- | --- |
| Cation | IC50 PLK1 | IC50 Scr. | IC50 PLK1 | IC50 Scr. | inhibition |
| CholGUA | 93 | 160 | 146 | 146 | not potent |
| CHIM | 160 | 160 | 146 | 146 | not potent |
| DC-Chol | 101 | 109 | 146 | 146 | not potent |
| MPDACA | 27 | 154 | 146 | 146 | not potent |
| GUADACA | 22 | 69 | 95 | 146 | 4 |
| BADACA | 99 | 160 | 146 | 146 | not potent |
| PONA | 30 | 100 | 70 | 99 | 2 |
| DOTAP | 160 | 160 | 146 | 146 | not potent |
| DODAP | 160 | 160 | 146 | 146 | not potent |

What is claimed is:

1. Lipid assemblies, comprising: anionic and cationic amphiphiles, and a neutral lipid,
   wherein the cationic amphiphiles are selected from the group consisting of structures (11), (12), and (15):

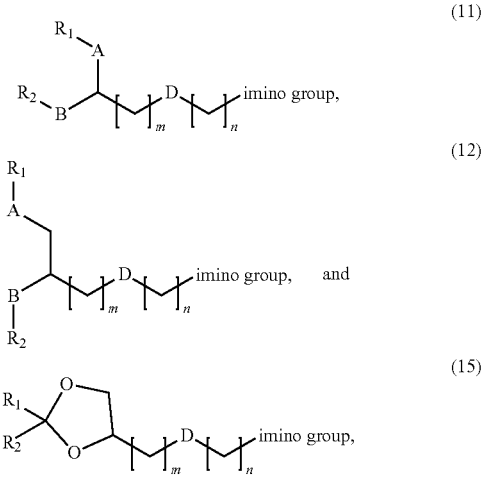

wherein:
   $R_1$ and $R_2$ are each independently alkyl, alkenyl, or alkynyl, wherein the alkyl, alkenyl, or alkynyl has 8 to 24 carbon atoms and 0, 1, or 2 unsaturated bonds;
   A and B are each independently absent, —$CH_2$—, —CH=, =CH—, —O—, —NH—, —C(O)—O—, —O—C(O)—, —O—C(O)—NH—, or —NH—C(O)—O—;
   D is absent, —$CH_2$—, —CH=, =CH—, —O—, —NH—, —C(O)—O—, —O—C(O)—, —C(O)—NH—, —NH—C(O)—, —O—C(O)—NH—, —NH—C(O)—O—,
   m is an integer between 0 and 29;
   n is an integer between 0 and 29; and
   the imino group comprises a guanido moiety, wherein the imino group is substantially charged under physiological conditions;
   wherein the anionic amphiphiles are carboxyl or phosphate lipids, and
   wherein the charge ratio between the cationic and anionic amphiphiles is from 0.67 to 1.5.

2. The lipid assemblies of claim 1, wherein the charge ratio between the cationic and anionic amphiphiles is from 1 to 1.5.

3. The lipid assemblies of claim 1, wherein the charge ratio between the cationic and anionic amphiphiles is from 1 to 1.22.

4. The lipid assemblies of claim 1, wherein the lipid assemblies are pH-sensitive, have negative to neutral surface charge under physiological conditions, and mediate cell transfection in the presence of serum.

5. The lipid assemblies of claim 1, wherein the anionic amphiphiles are carboxyl lipids.

6. The lipid assemblies of claim 1, wherein the anionic amphiphiles are phosphate lipids.

7. The lipid assemblies of claim 1, wherein the imino group is:

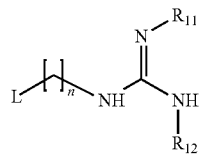

wherein $R_{11}$ and $R_{12}$ are, independently of each other, H, —$CH_3$ or —$CH_2CH_3$, n is 0 or 1, and L is an apolar region of the cationic amphiphile.

8. The lipid assemblies of claim 1, wherein the cationic amphiphiles are GUADACA.

9. The lipid assemblies of claim 1, wherein the anionic amphiphiles are selected from the group consisting of CHEMS, DMGS, DOGS, DOPA and POPA.

10. The lipid assemblies of claim 1, wherein the neutral lipid is selected from the group consisting of cholesterol, phosphatidylcholine, phosphatidylethanolamine, and mixtures thereof.

11. The lipid assemblies of claim 10, wherein the neutral lipid is cholesterol, and the molar fraction of cholesterol in the lipid assemblies is from 10 to 50 mol %.

12. The lipid assemblies of claim 1, further comprising PEG lipids.

13. The lipid assemblies of claim 1, wherein the charge ratio between the cationic and anionic amphiphiles is 1 or less and wherein no PEG lipids are present.

14. The lipid assemblies of claim 1, further comprising nucleic acid.

15. The lipid assemblies of claim 14, wherein the nucleic acid is an oligonucleotide.

16. The lipid assemblies of claim 14, wherein the nucleic acid is polynucleotide, DNA plasmid, linear DNA construct or mRNA.

17. The lipid assemblies of claim 1, wherein the charge ratio between the cationic and anionic amphiphiles is from 0.67 to 1.25.

18. The lipid assemblies of claim 1, wherein the guanido moiety is selected from the group consisting of:

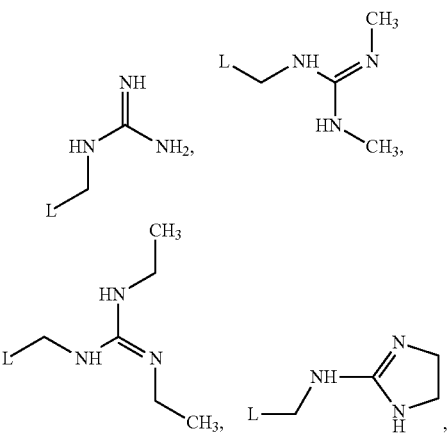

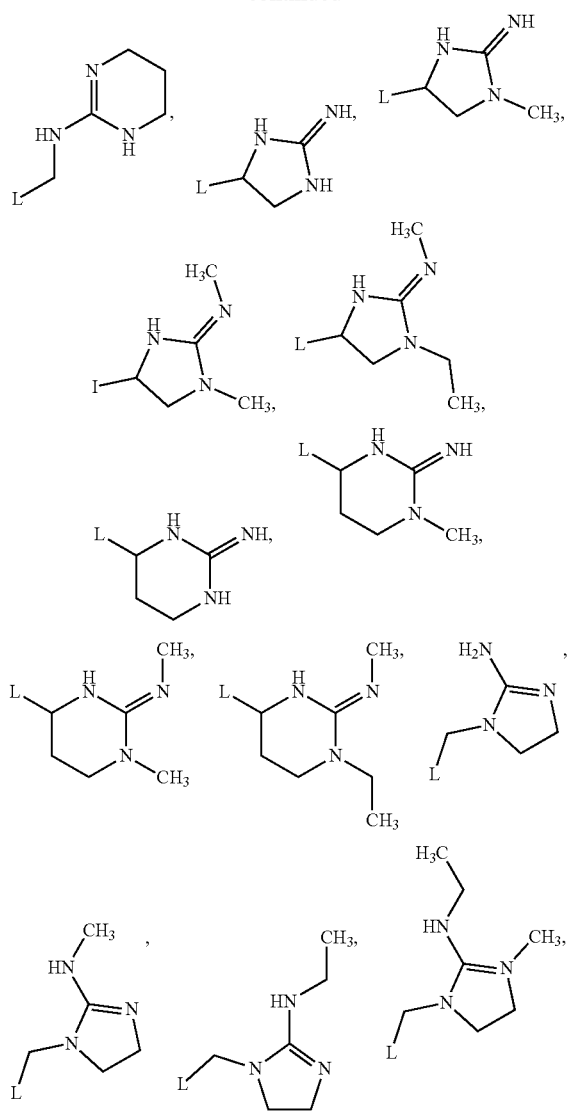
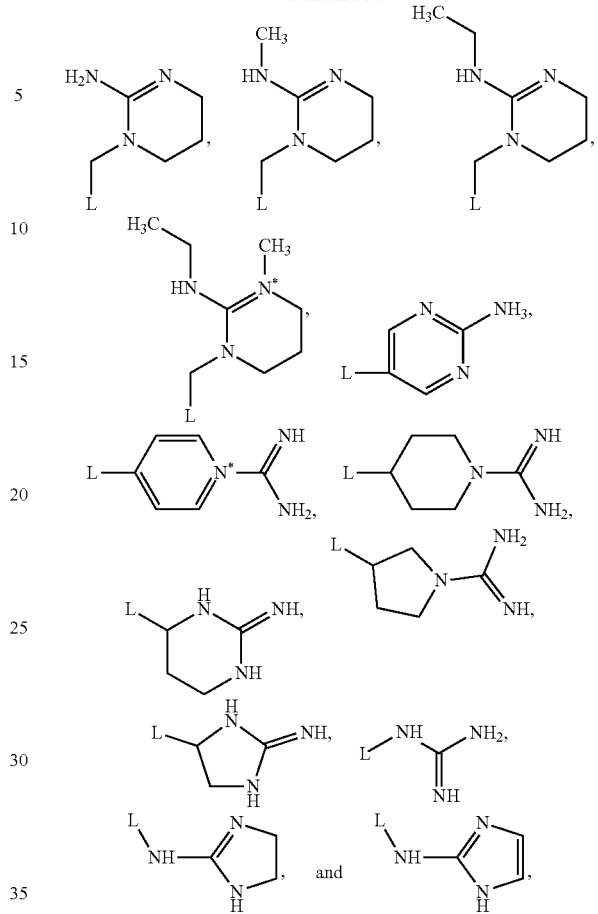
wherein L is an apolar region of the cationic amphiphile.
19. A method of transfecting cells, comprising applying the lipid assemblies of claim 1 to the cells in the presence of serum.
20. The method of claim 19, further comprising applying the lipid assemblies into bloodstream.
* * * * *